United States Patent
Thomas et al.

(10) Patent No.: US 6,758,953 B2
(45) Date of Patent: Jul. 6, 2004

(54) MULTISTAGE ELECTROPHORESIS APPARATUS AND METHOD OF USE FOR THE SEPARATION AND PURIFICATION OF CELLS, PARTICLES AND SOLUTES

(76) Inventors: Nathan A. Thomas, 3100 Rockaway Dr., Louisville, KY (US) 40216; John C. Vellinger, 2979 N. Luther Rd., Floyd Knobs, IN (US) 47119; Paul W. Todd, 7332 Wind Dance Pkwy., Greenville, IN (US) 47124; Shramik Sengupta, 912, 21st Ave. S., #210, Minneapolis, MN (US) 55404

( * ) Notice: Subject to any disclaimer, the term of this patent is extended or adjusted under 35 U.S.C. 154(b) by 131 days.

(21) Appl. No.: 10/136,176

(22) Filed: Apr. 29, 2002

(65) Prior Publication Data

US 2003/0019817 A1 Jan. 30, 2003

Related U.S. Application Data

(63) Continuation-in-part of application No. PCT/US00/29997, filed on Oct. 30, 2000, and a continuation-in-part of application No. 09/702,557, filed on Oct. 31, 2000, now abandoned.
(60) Provisional application No. 60/162,319, filed on Oct. 28, 1999, and provisional application No. 60/163,667, filed on Nov. 5, 1999.

(51) Int. Cl.[7] .................. B01D 57/02; C02F 1/469; G01N 27/26; G01L 1/20; C25B 15/00
(52) U.S. Cl. .............. 204/450; 435/6; 436/526; 204/465; 204/600; 204/554; 204/571
(58) Field of Search ................. 204/465, 600, 204/450, 554, 571

(56) References Cited

U.S. PATENT DOCUMENTS

| 3,755,121 A | 8/1973 | Schultz |
| 4,427,294 A | * 1/1984 | Nardo ............ 356/344 |
| 4,631,120 A | 12/1986 | Pohl |
| 4,654,132 A | 3/1987 | Takagi et al. |
| 4,690,749 A | 9/1987 | Van Alstine et al. |
| 4,715,943 A | 12/1987 | Place et al. |
| 4,859,301 A | 8/1989 | Brenner et al. |
| 4,874,507 A | 10/1989 | Whitlock |
| 4,997,536 A | 3/1991 | Ohms et al. |
| 5,041,203 A | * 8/1991 | Serwer ............ 204/457 |

(List continued on next page.)

OTHER PUBLICATIONS

K.D. Cole, P. Todd, K. Srinivasan, B.K. Dutta, "Free–solution Electrophoresis of Proteins in an Improved Density Gradient Column and by Capillary Electrophoresis", Journal of Chromatography A, 707 (1995) 77–85.

(List continued on next page.)

Primary Examiner—Mark L. Bell
Assistant Examiner—Jennine Brown
(74) Attorney, Agent, or Firm—Carrithers Law Office; David W. Carrithers

(57) ABSTRACT

An electrophoresis device is disclosed which separates cells, particles, proteins and other separands by collecting samples of decreasing electrophoretic mobility in a train of inverted cavities while an electric field is applied between said inverted cavities and one or more sample cuvettes containing a mixture of cells, particles, proteins or other separands. One circular plate is provided for the one or more sample cuvettes, and one circular plate is provided for the multiple collection cavities. The invention utilizes an innovative purification method that combines free electrophoresis and multistage extraction in an instrument capable of separating living cells, particles, and proteins in useful quantities at high concentrations. The purification method includes a method for dealing with electrolysis products, a technique for controlling the electrical energy input, and an approach for keeping the process isothermal. The invention solves many separation applications problems on earth and also in reduced gravity in space flight.

42 Claims, 22 Drawing Sheets

U.S. PATENT DOCUMENTS

| | | | |
|---|---|---|---|
| 5,069,768 A | 12/1991 | Plaas-Link | |
| 5,082,548 A | 1/1992 | Faupel et al. | |
| 5,087,695 A | 2/1992 | McAuley | |
| 5,242,568 A | 9/1993 | Ehr et al. | |
| 5,277,774 A | 1/1994 | Shmidt et al. | |
| 5,562,812 A | 10/1996 | Carlson et al. | |
| 5,656,146 A | 8/1997 | Day et al. | |
| 5,798,032 A | 8/1998 | Khan et al. | |
| 5,837,115 A | 11/1998 | Austin et al. | |
| 5,851,370 A | 12/1998 | Maracas et al. | |
| 5,853,668 A | 12/1998 | Begg et al. | |
| 5,916,426 A | 6/1999 | Madabhushi et al. | |
| 5,972,188 A | 10/1999 | Rice et al. | |
| 6,059,948 A | 5/2000 | Updyke et al. | |
| 6,312,910 B1 * | 11/2001 | Vellinger et al. | 435/6 |

OTHER PUBLICATIONS

J.P. Agarwala, "Inclined Settler Classification of Particles and Transport of Ions through Liquid Membranes with an Electric Field", PhD Thesis, University of Colorado, Boulder, 1994.

P.A. Albertsson, "Partition of Cell Particles and Particles and Macromolecules", Third Ed., John Wiley and Sons, New York, 1986.

Tulp, et al "Preparative Density Gradient Electrophoresis of Cells and Cell Organelles", Electrophoresis, 1982, pp. 317–324.

Abstract published in Japanese Journal of Electrophoresis vol. 43, No. 1. by Todd P., Raghavarao, K.S.M.S., Sengupta S., Doyle J.F., Vallinger J., and Deuser M.S. for Seminar presentation given at Meeting of the International Counsel of Electrophoresis Societies (ICES'99) in Tokyo, Japan from May 25–28, 1999 entitled *Multistage Electrophoresis and Magnetic Separation of Cells, Particles, and Solutes*; and.

Journal Publication by Todd P., Raghavarao, K.S.M.S., Sengupta S., Doyle J.F., Vallinger J., and Deuser M.S. for "Multistage Electrophoresis", Electrophoresis 2000, vol. 21, pp. 318–324 which is the publication of the material presented in the Meeting of the International Counsel of electrophoresis Socieites in Tokyo, Japan referenced above.

* cited by examiner

Pseudo-equilibrium plot incorporating the effects of mixing (mobility ratio = 0.3; first mixing ratio = 0.3; second mixing ratio = 0; third mixing ratio = 0.10)

Schematic representation of the migration of particles of a single type from the original cavity to a series of cavities during the application of a fixed electric field for a fixed period of time per stage (constant Et), representing the constant-field operating model.

Equilibrium lines for the separation of two separands having the indicated mobility ratios using the pseudoequilibrium model. Y = particle fraction in the extract. X = particle fraction in the feed. $\mu_B/\mu_A$ = mobility ratio.

Purity resulting from application of the pseudoequilibrium model to the separation of two particle types with the given mobility ratios.
Dashed line, ideal system; solid line, real system accounting for non-electrophoretic mixing due to sliding plates.

MULTISTAGE ELECTROPHORESIS APPARATUS AND METHOD OF USE FOR THE SEPARATION AND PURIFICATION OF CELLS, PARTICLES AND SOLUTES

This application is a Continuation In Part application claiming priority from copending PCT Application Serial No. PCT/US00/29997 filed on Oct. 1, 2000; now abandoned and U.S. Utility application Ser. No. 09/702,557 filed on Oct. 30, 2000 which are hereby incorporated by reference herein.

This application also claims priority from copending U.S. Provisional Application Serial No. 60/162,319 filed on Oct. 28, 1999; U.S. Provisional Application Serial No. 60/163,667 filed on Nov. 5, 1999 which are hereby incorporated by reference herein.

This application is part of a government project, Contract No. NAS9-97088.

FIELD OF THE INVENTION

The invention relates to the field of combining free electrophoresis and multistage extraction in an instrument capable of separating living cells, particles, proteins, and solutes in useful quantities at high concentrations.

DESCRIPTION OF THE PRIOR ART

Conventional particle separation techniques typically include centrifugation, which is limited due to its specificity, capacity, speed, energy consumption, biological impact, and microgravity environment disturbances.

Electrophoresis is a leading method for resolving mixtures of cells or charged macromolecules (proteins and nucleic acids). The electrophoretic separation of proteins without gels has been a long-standing goal of separations research. The process of electrophoresis has so far been unable to "graduate" from an analytical tool to a viable unit operation. This is primarily because of various problems such as thermal convection, electro osmosis, particle sedimentation, droplet sedimentation, particle aggregation, and electro hydrodynamic zone distortion have been found to be major obstacles to scale-up. The traditional approach has been to devise density gradients or elaborate flowing devices to counteract these problems; however incorporation of such methods has been unable to address these problems effectively. Also, their addition has caused the process to become cumbersome, thus further reducing the appeal of electrophoresis.

Without the need to prepare density gradients and/or use elaborate flowing systems, free electrophoresis can enjoy much more widespread use because it is a high-resolution method that does not require adsorption to solid media and the subsequent solids handling. It can separate both particles (cells) and solutes (macromolecules) with equal ease. Some specific applications for electrophoresis include the separation of different cells of peripheral blood and bone marrow in hematological and immunological research. Other potential applications include clinical therapeutics and the separation of proteins from body fluids, tissue extracts and fermentation broths.

A mixing problem encountered during free electrophoresis is the mixing caused by the release of gases at the electrodes. However, the use of either non-gassing electrodes such as described in (Agarwala 1994) and incorporated herein or membrane-separated electrodes such as described in (Cole et. al. 1995) and incorporated herein will effectively solve this problem. Experiments performed using palladium electrodes have demonstrated our ability to solve this problem.

Free electrophoresis is a process in which a sample is introduced into a liquid buffer, static or flowing, in a zone and subjected to an electric field in which separands migrate according to their surface charge properties. Fluid instabilities result because longer migration paths are exposed for longer times to developing instabilities.

Timmerman A. Tulp and M. G. Barnhoorn in *Preparative Density Gradient electrophoresis of Cells and Cell Organelles A New Separation Chamber, Electroporesis* (1982), teaches that a short electrophoretic migration path in a non-moving buffer avoids exposure of migrating separands to unstable buffer flows. Tulp designed a reorienting, free electrophoresis device consisting of a flat disk-shaped container with thin sample bands and a short vertical migration distance. The bottom and the top electrode fluids served as the coolant, the total height of the separation column was 1–2 cm, and its diameter was greater than 15 cm. The distance between the unrelated separands was 1–2 mm, and this distance was increased during fractionation after electrophoresis by re-orienting the disk so that it became a narrow vertical column.

In a different field of separations, Albertsson et al. teaches that multistage extraction processes can proceed in a multistage separator consisting of two sets of cavities facing each other around the periphery of a pair of plates. Further, conventional electrophoresis devices rely on the use of gels, paper or flowing channels to stabilize the electrophoresis buffer in which separands migrate. The devices are limited in capacity and, in the case of flowing channels, difficult for the user to operate and maintain. Obviously, prior art is not meeting the needs of separations by free electrophoresis. Further, applications of free electrophoresis in low gravity require a gravity independent means of collecting electrophoretically separated fractions of the sample.

The present invention fulfills this requirement and is hence ideal for applications in space-flight electrophoresis experiments and applications. For instance, the overall efficacy of electrophoresis as a unit operation can be greatly improved if the migration distance is greatly reduced and the process is multistaged.

SUMMARY OF THE INVENTION

A thin-layer countercurrent distribution apparatus is designed and constructed so that up to 20 fractions can be collected on the basis of electrophoretic mobility by application of an electric field. The multistage electrophoretic separation and purification of cells, particles, proteins, and solutes utilize an innovative purification method that combines free electrophoresis and multistage extraction in an instrument capable of separating and/or purifying living cells, particles and proteins in useful quantities and at high concentrations. The mixture to be separated starts in a bottom cavity, and successive top cavities, collect fractions as separand particles or molecules are electrophoresis upward out of the bottom cavity. Mathematical models of this process have been developed, and experiments performed to verify the predictions of the models by collecting and counting particles in each cavity after fractionation. The process depends on the electrophoretic mobility of separands, and is gravitationally stabilized so that it functions in laboratories on earth and in space.

Moreover, an electrophoresis device is disclosed which separates cells, particles, proteins and other separands by collecting samples of decreasing electrophoretic mobility in a train of inverted cavities while an electric field is applied between said inverted cavities and one or more sample cuvettes containing a mixture of cells, particles, proteins or other separands. One circular plate is provided for the one or more sample cuvettes, and one circular plate is provided for the multiple collection cavities. The invention utilizes an innovative purification method that combines free electrophoresis and multistage extraction in an instrument capable of separating living cells, particles, and proteins in useful quantities at high concentrations. The purification method includes a method for dealing with electrolysis products, a technique for controlling the electrical energy input, and an approach for keeping the process isothermal. The invention solves many separation applications problems on earth and also in reduced gravity in space flight.

The multistage electrophoretic purification of cells, particles, and proteins, utilizes an innovative purification method that combines free electrophoresis and multistage extraction in an instrument capable of separating living cells, particles and proteins in useful quantities and at high concentrations. The isothermal process depends on the electrophoretic mobility of separands, and is gravitationally stabilized so that it functions in laboratories on earth and in space. The purification method includes a method for dealing with electrolysis, a technique for transporting and varying electrical energy, and an approach for keeping the process isothermal. The electrophoretic technology resolves many unique separation applications on earth as well as in reduced gravity environments in space flight.

The instant invention is extremely well suited to immunological research, pharmaceutical delivery, biomedical applications, cell biology, and cell separation problems associated with clinical, animal, and plant research. The separation process is well suited to space flight, specifically for on-orbit cell separation problems associated with biological research. Moreover, the electrophoretic technology and electrokinetic separation employ affinity partitioning and electrophoresis. The invention incorporates both features, a short migration distance, and a multistage operation technique in order to increase the throughput of the process and to make the process easier to operate.

The multistage electrophoresis separation and purification assembly utilizes oppositely charged electrodes at the ends of two cavities providing the electric driving force for the migration of particles. It provides a thin layer countercurrent distribution apparatus capable of collecting up to 22 fractions by applying an electric field. The hardware is a combination of free electrophoretic and multistage extraction and consists of 20 or more cavities of a multistage thin layer extraction system. Half cavities oppose each other in disks that are sealed together and one disk rotates with respect to each other. The mixture to be separated starts in a single cavity on a first plate, and successive cavities collect fractions as separand particles or molecules are electrophoresed upward out of the cavity of a second plate. The half cavities are disk shaped, the top cavities having flat tops and the bottom cavities having flat bottoms. Both consist of palladium metal electrodes that produce an electric field when the two cavities re in contact. Each half cavity is only a fee millimeters in height so that the fluid within it remains isothermal during the application of an electric field that transfers separand particles or molecules from the cavity of one plate to the cavity of the corresponding plate.

As each separand is transferred to a new cavity it is swept into the upper half by the electric field or left in the lower half, depending on its electrophoretic mobility. The first fractions collected into the top cavity consist of high mobility separands while later fractions consist of lower mobility solutes or particles. The resulting fractogram corresponds linearly to an electrophoretic mobility distribution. The unit can be operated in various modes such as skimming separands from the top of a single bottom cavity without mixing, or following a true counter-current separation with or without remixing at each stage. A mathematical model, from which distributions and resolution can be derived was formulated, and its predictions tested in multistage experiments.

It is an object of the invention to provide a device for the successful electrophoretic separation of cells, particles, proteins and other separands It is an object of the present invention to provide a temperature control system capable of controlling the temperature from $-37°$ C. to $20°$ C. and preferably at about $4°$ C.

It is an object of the present invention to provide a sample collection capability of one or more independent samples.

It is an object of the present invention to provide a means for holding the magnitude of the electric field is held constant at a selected field strength by a microprocessor-controlled electric circuit, It is an object of the present invention to provide a means of collecting different types of cells or to collect only cells or particles, only media, or both.

It is an object of the present invention to provide a capability to separate cells from culture medium for sampling.

It is an object of the present invention to provide a medium which is replenishable by means of perfusion which is programmable or active on demand.

It is an object of the present invention to provide as an option a electromagnetic stirring system.

It is an object of the present invention to provide a means of providing the apparatus in a modular cassette in order to facilitate sequential experiments.

It is an object of the present invention to provide a means for the researcher to have experiment flexibility and select solutions, temperatures, and sampling times.

It is an object of the present invention to provide a means for collecting samples of cells, particles, or medium in bags, cuvettes, syringes, or other vessels.

It is an object of the present invention to provide a purification process in which a low conductivity separating buffer is used and electrode metals are selected to prevent gas bubble release and minimize or eliminate the need for active cooling.

It is an object of the present invention to provide a high conductivity separating buffer and receiving electrode metals are selected to prevent gas bubble release, and the one feed cavity electrode is separated from the feed sample cavity by an ultrafiltration membrane and contains an electrolyte that is pumped therethrough.

It is an object of the present invention to provide a multistage electrophoretic separation and purification system designed to be utilized in a cassette integrated within an space flight processing facility.

These and other objects of the present invention will be more fully understood from the following description of the invention.

A preferred embodiment of the present invention provides a multistage electrophoretic purification process for separating and purifying cells, particles, and proteins, and includes a frame and opposing circular plates defining a stationary sample plate containing particles to be separated in a fluid and a rotating collection plate in cooperative sealable engagement with one another, each one including at least one cavity alignable with one another. At least one stationary sample plate cavity and at least one rotating collection plate cavity are positionable for fluid communication with one another arranged to form a multi-stage thin-layer extraction system. At least one stationary sample plate cavity and at least one collection plate cavity contains a metal electrode for producing an electric field in the fluid subjecting the particles to be separated to the electric field separating the particles by their degree of electrophoretic mobility causing migration of the particles and collecting the particles in at least one collection cavity. Upon complete separation the electric field is de-energized and the plates are rotated countercurrently until the upper cavity aligns with a lower cavity with fresh solution that is thoroughly mixed with the separated cells or molecules, and the process is repeated as many times as necessary to effect the desired separation.

A preferred method of separating cells, particles, proteins and other separands with an electrophoresis device comprises the steps of placing a sample of particles to be separated comprising cells, media, proteins or other separands, or mixtures thereof into at least one sample container containing an fluid and supported by means for holding. Rotate a collection plate having at least one collection cavity in sealed cooperative engagement with the at least one sample container. Align the at least one collection cavity with the at least one sample container providing fluid communication therewith. Apply an electric current field to the sample in the at least one sample container while the at least one collection cavity is in fluid communication therewith. Collect a fraction of the sample containing particles to be separated having a different electrophoretic mobility in the at least one collection cavity while the electric field is applied thereto.

BRIEF DESCRIPTION OF THE DRAWINGS

A better understanding of the present invention will be had upon reference to the following description in conjunction with the accompanying drawings in which like numerals refer to like parts throughout the several views and wherein.

DESCRIPTION OF THE PREFERRED EMBODIMENT

Figure 1:
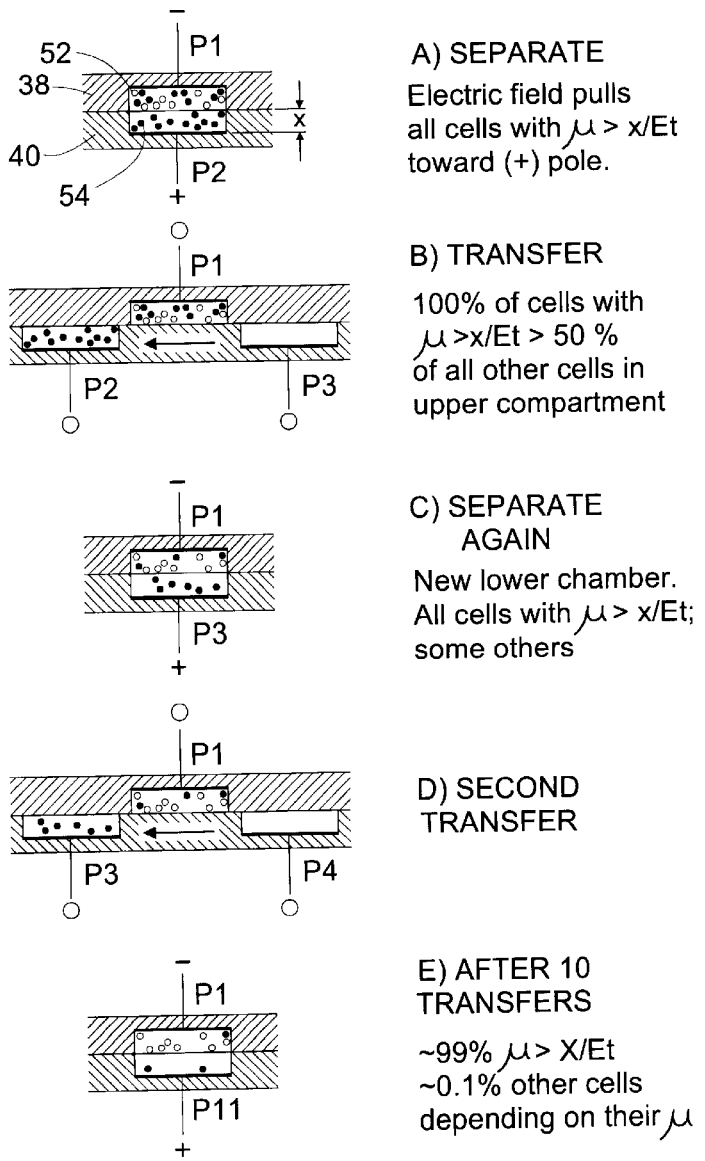
FIG. 1 is a flow diagram showing a single stage of the multistage electrophoretic process where $\mu$ is the electrophoretic mobility of a particle, E is the electric field strength, and t is time.

The multistage electrophoresis apparatus and method of use for the separation and purification of cells, particles, and solutes is generally designated 30 in the drawings. The individual components of the device 30 will first be identified and the operating parameters and methods of use will be described thereafter.

Figure 2:
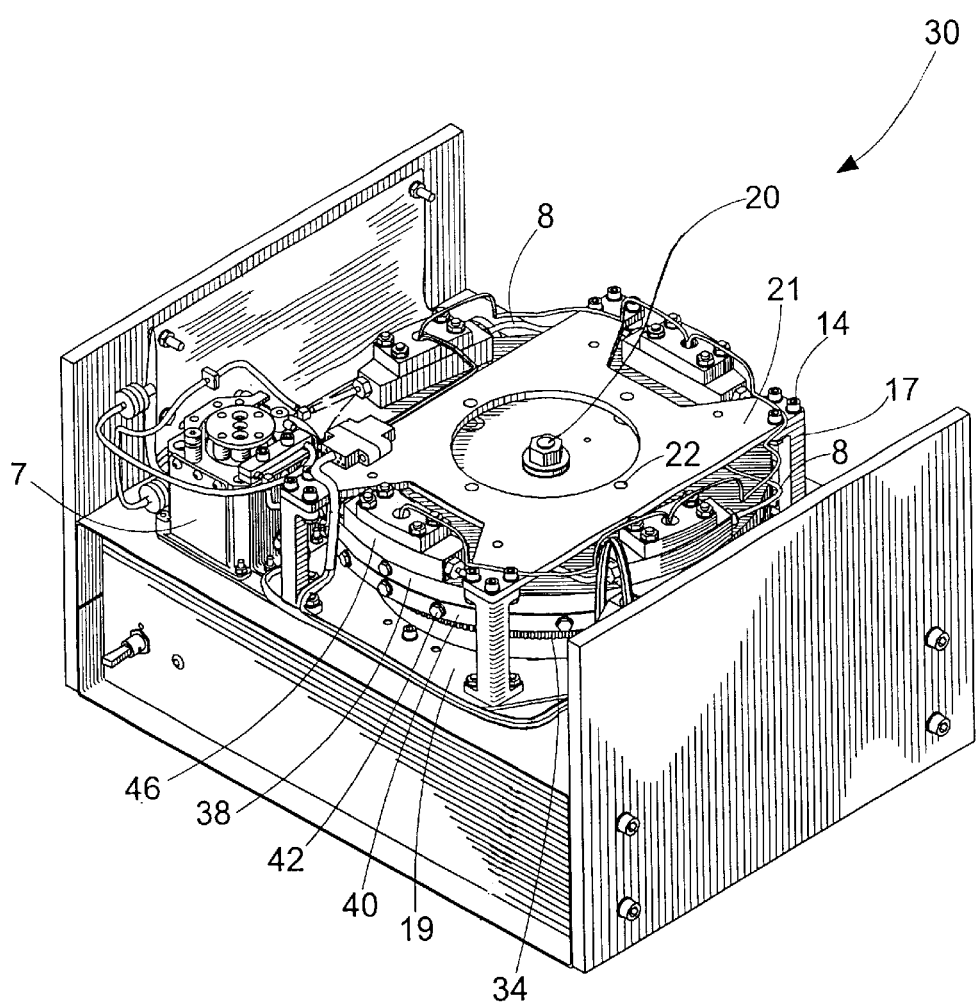
FIG. 2 is a perspective view of a multistage electrophoresis device.
Figure 3:
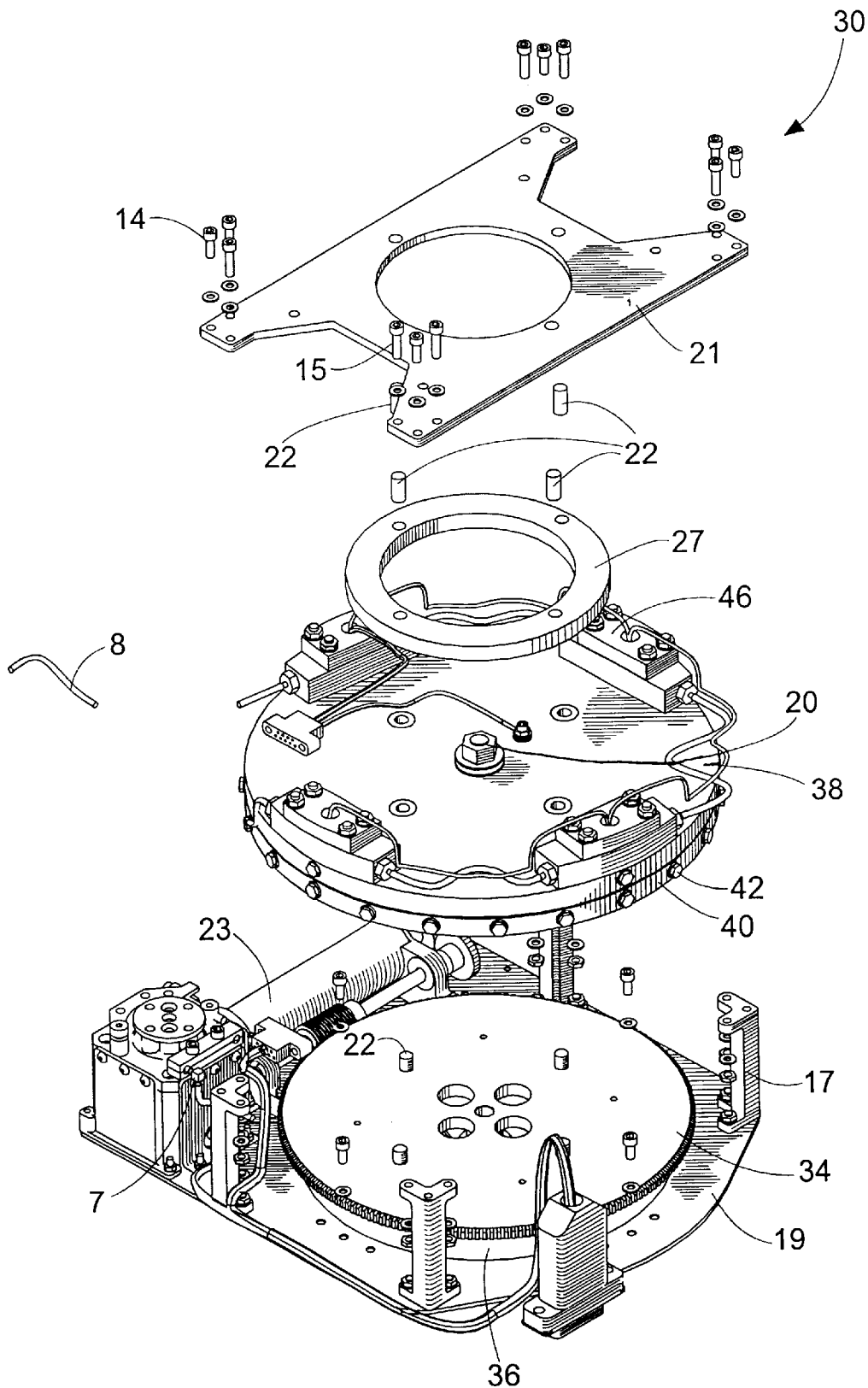
FIG. 3 is an exploded view illustrating the components of the device shown in FIG. 2.
Figure 4:
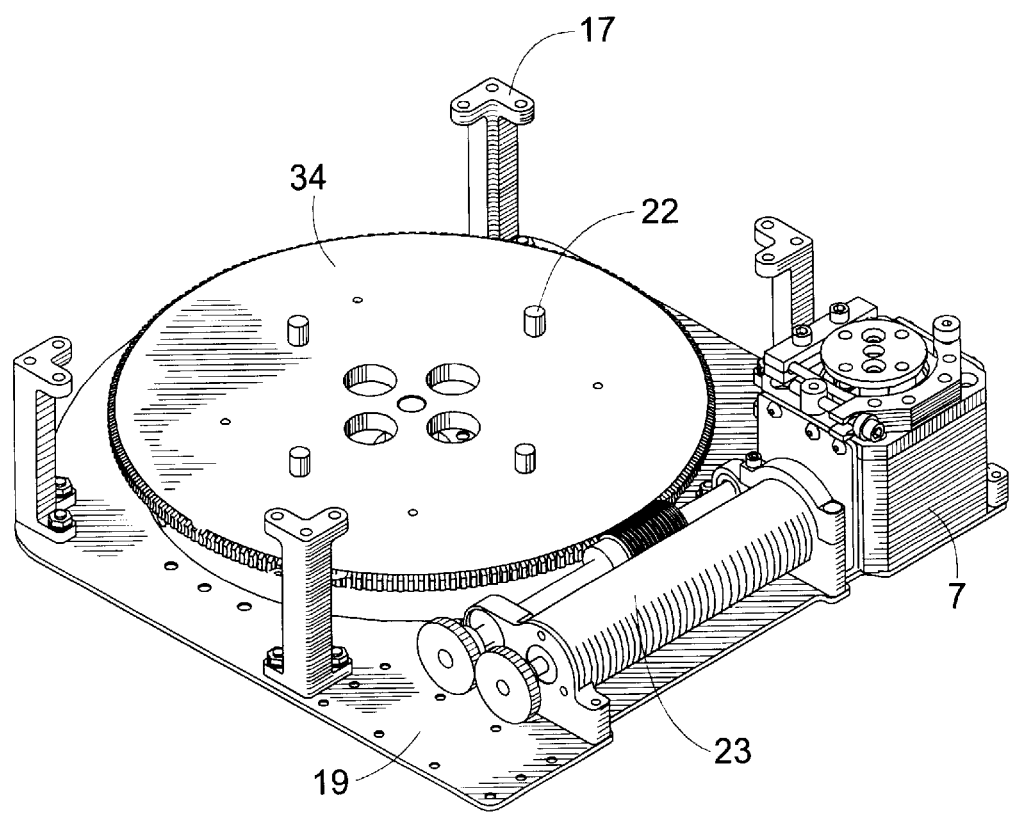
FIG. 4 is a perspective view of the rotating mechanisms of the device shown in FIG. 2.
Figure 5:
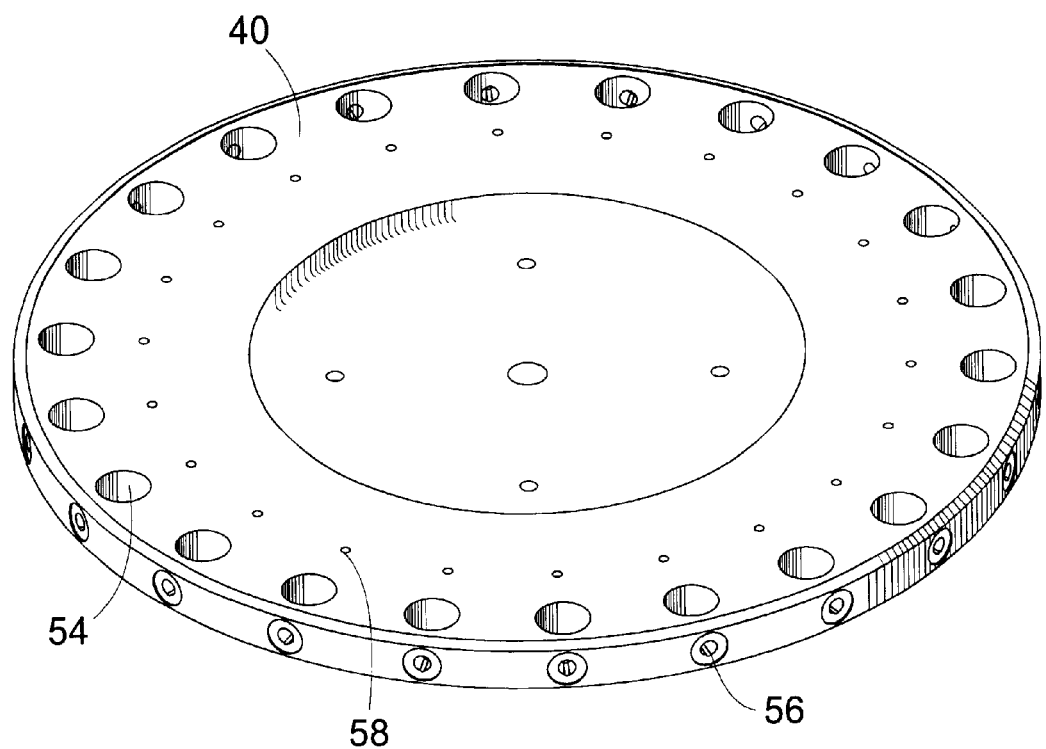
FIG. 5 is a perspective view of the rotating sample-collection plate of the device shown in FIG. 2.
Figure 6:
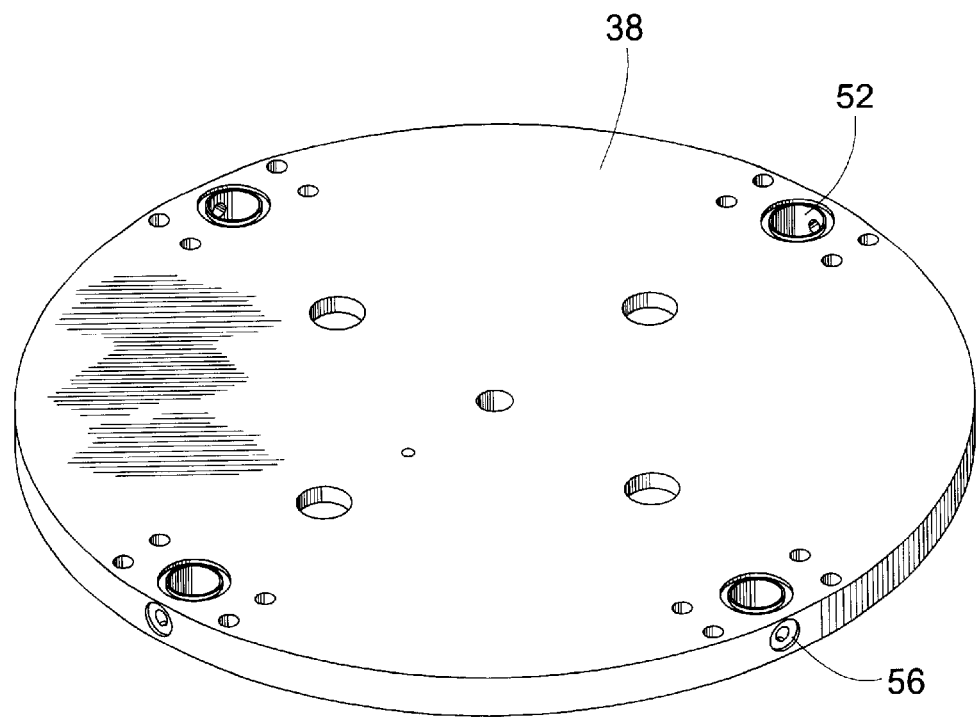
FIG. 6 is a perspective view of the stationary sample-feed plate of the device shown in FIG. 2.
Figure 9:
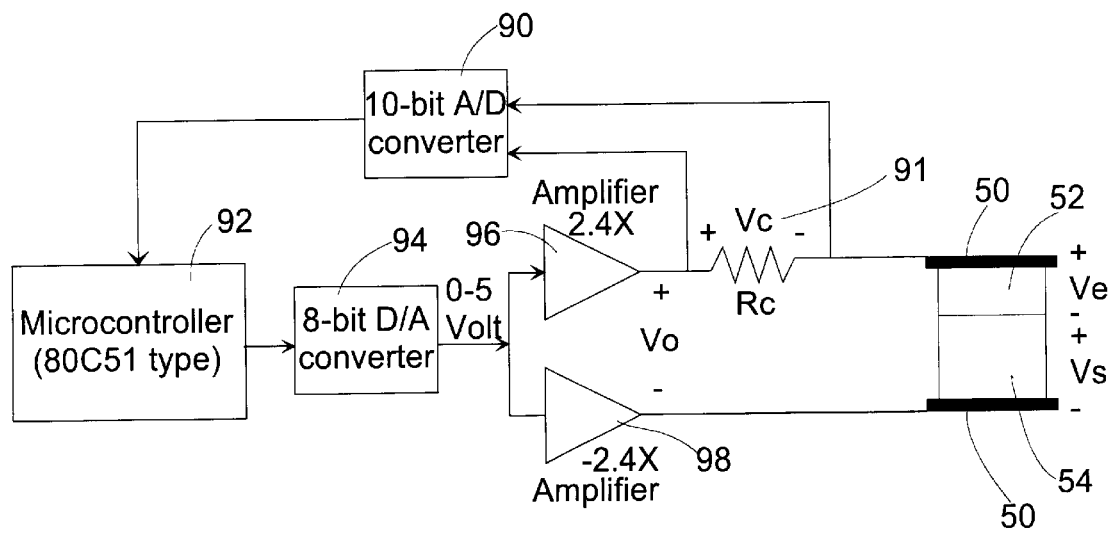
FIG. 9 is a circuit diagram of a field-regulation circuit for maintaining constant field across the pair of cavities shown in FIG. 7.
Figure 10:
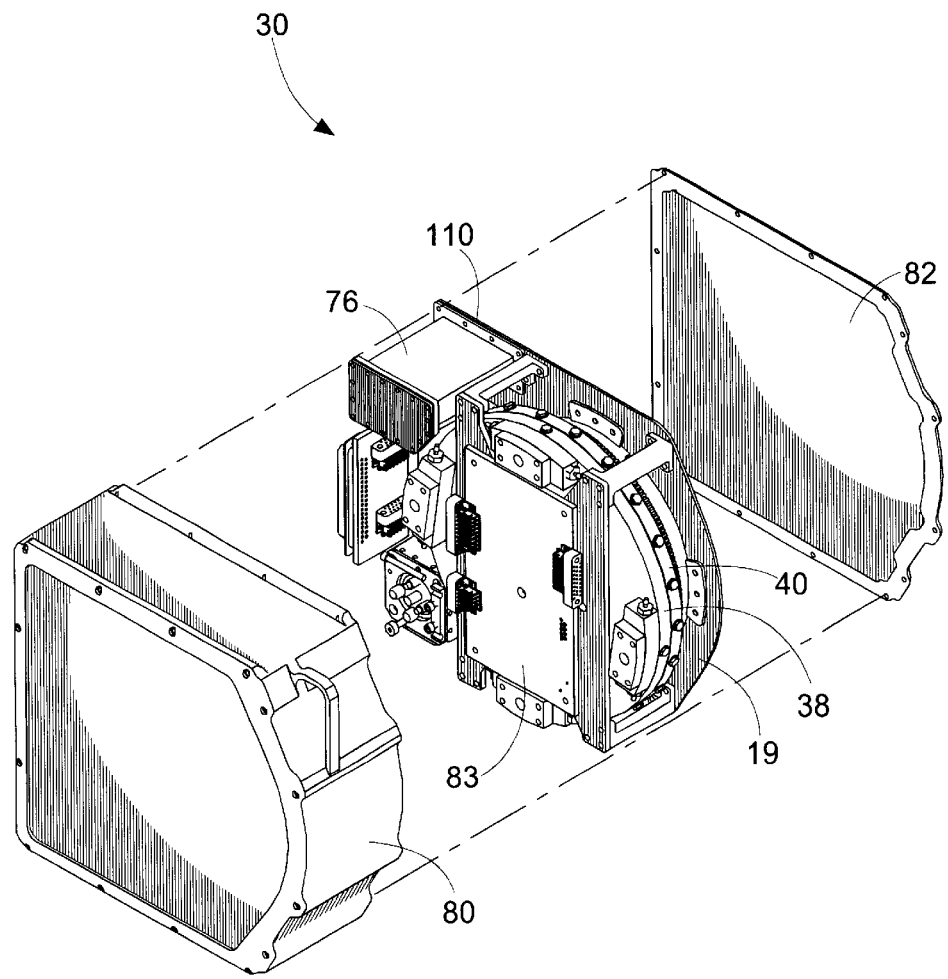
FIG. 10 is an exploded view, in perspective, of an embodiment of the device of FIG. 2 adapted for functioning in space flight showing the electrophoretic device nested within a cassette assembly which is inserted within a containment enclosure.

The multistage electrophoresis device is generally designated 30 in FIGS. 2, 3 and 10 of the drawings. The individual components of the device 30 will first be identified and the operation of, and fluid flow through device 30 will then be described. Multistage electrophoresis device 30 includes a base 19 with a support framework 17 extending upwardly therefrom. Top cover holding plate 21 is attached to support framework 17 opposite base 19. A stationary sample plate 38 is attached and held in position by cover plate 21. In a preferred embodiment, the stationary sample plate 38 is manufactured of a non-conducting material, preferably a polymer, and has four cavities 52 for the containment of feed samples. (At least one cavity is required). An electrolyte compartment 46 is fastened above each of four cavities (representing four sample cuvettes) 52 for the containment of conducting solution 62, which conducting solution is also known as electrolyte. Each electrolyte compartment 46 is separated from its respective sample cuvettes 52 by a hydrophilic polymeric membrane 60, the membrane having a molecular-weight cutoff of 1,000. Each electrolyte compartment 46 contains a circular noble-metal electrode and is perforated on two sides by tubing connectors that carry flowing electrolyte 62 from electrolyte reservoir 76 via polymeric tubing 8 to all four electrolyte compartments 52 connected in series to electrolyte reservoir 76, the electrolyte reservoir containing hydrophilic polymeric membrane 74 which cleans the circulating electrolyte 62. Electrolyte also passes through a vapor release having hydrophilic membrane filter 71 through which gas bubbles are released via opening 72 which is open to the ambient environment. Stationary sample plate 38 is held in downward compression by Belleville spring action applied by pressure ring 27 via the tension on machine screws 14 which hold down cover plate 21 such that fluid leakage between upper stationary sample plate 38 and lower rotating sample plate 40 is prevented. Upper sample plate 38 is prevented from rotating by four pins 22, the pins penetrating cover plate 38, pressure ring 27 and upper sample plate 38. Lower rotating sample plate 40 is attached by four machine screws 16 to rotating gear wheel 34 and caused to rotate with the gear wheel by four pins 22, the gear wheel being caused to rotate by worm-drive motor 23 when commanded to do so by an incoming computer-generated signal. Lower sample plate 40 contains at least one and as shown in a preferred embodiment twenty-two (22) more-or-less sample collection cavities 54 each the sample cavity having a fill port 56 sealed by a fill-port plug 42, a noble-metal electrode 50, and a conducting wire which penetrates hole 58 to carry current to the noble-metal electrode. As shown best in FIG. 14, the top plate 38 and bottom plate 40 contain corresponding cooperatively engaging cavities providing a seal, wherein the top plate 38 is covered with a noble metal electrode 50 held in place by a gasket 47 and cover 49 which is held in place by a plurality of screws 51. Support framework 17 separates the above-described upper plate assembly from the above-describe lower plate assembly. The current between noble-metal electrodes 50 in the upper stationary cuvettes or cavities 52 and the rotating cavities 54, respectively, through electrophoresis buffer 62 is controlled by a control circuit shown in FIG. 9 of the drawings such that the electric field between the electrodes, in volts per meter, is held constant at a value chosen by the operator. The electric field is held between positive 96 and negative 98 amplifiers, which receive an analogue signal between 0 and 5 volts from microcomputer 92 (in this embodiment, Siemens C505 digital micro controller) via digital-to-analogue converter 94. The current passing through load resistor 91 governs the signal to microcomputer 92 via analogue-to-digital converter 90.

PROCESS AND METHOD OF USE

Figure 14:
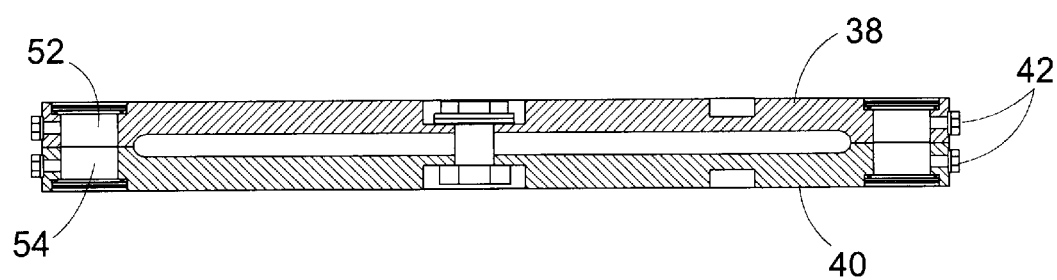
FIG. 14 shows a sectional side view of the top plate 38 and bottom plate 40 and cavities wherein the top is covered with a noble metal electrode held in place by a gasket and cover which is held in place by a plurality of screws.
Figure 15:
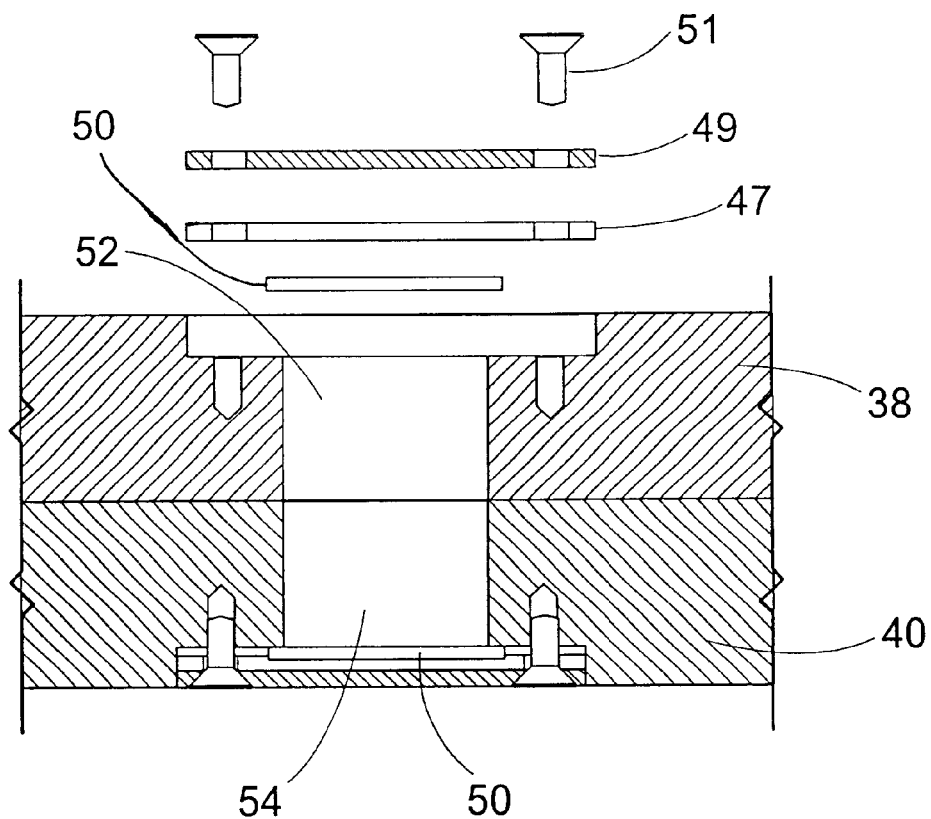
FIG. 15 shows a sectional view of the top cavity 52 and bottom cavity 54 of the plate of FIG. 14.
Figure 16:
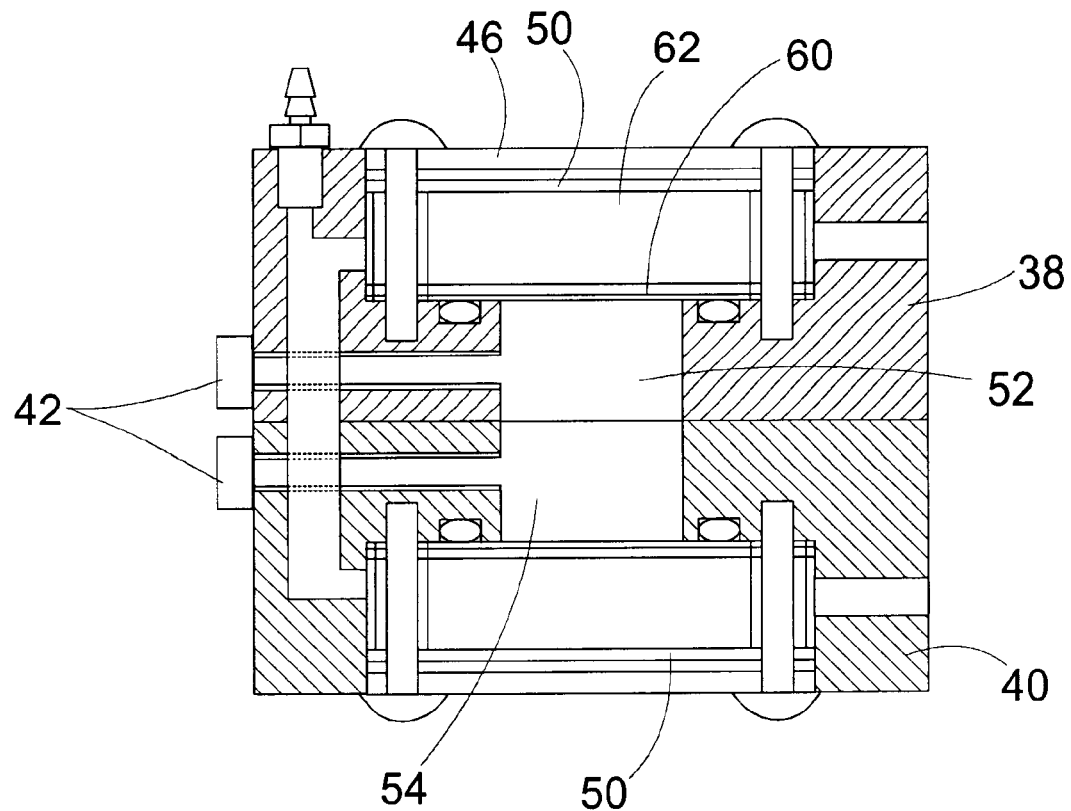
FIG. 16 is a sectional view of a portion of the top plate and the bottom plate showing the details of the cavity and fill ports.

The multistage electrophoresis device 30 must be capable of physically separating the sample at the conclusion of an experiment so that the sample may be analyzed when it is returned to the experimenters. This is accomplished by using the pair of plates or disks, defining a top stationary sample plate 38 and a lower rotating sample plate 40), formed from polycarbonate or other similar nonconducting material, that have spaced apart aligned cavities or voids formed therein for containing fluid samples cut into them. The plates 38, 40 could be formed or other materials preferably polymers. As shown, the cavities 52 form compartments, chambers or cuvettes in the top stationary sample plate 38. Movable cavities 54 form compartments in the rotary bottom plate 40 which contain the sample to be separated and are alignable with the cavities 52 in the stationary top plate 38. FIGS. 14 shows a side view of the top plate 38 and bottom plate 40, FIG. 15 shows a sectional view of the top cavity 52 and bottom cavity 54 of the plate of FIG. 14, FIG. 16 shows the details of the cavity and fill ports.

Although the cavities shown in the preferred embodiment are cylindrical in shape it is contemplated that they could be shaped having an elliptical, rectangular or pie shape as well depending upon the particular application. The plates 38 and 40 are cooperatively engaged and are able to both maintain a seal during rotation. A sealant such as a silicon grease of other nonvolatile and inert grease may be utilized therebetween at selected points, but is not required.

The process by which the cavities 52 align is illustrated in FIG. 1 which shows a single stage of the multistage electrophoretic process. In the embodiment shown, initially, movable cavity 54 contains the sample mixture to be separated. It is then brought into contact with buffer-containing stationary cavity 52, and an electric field is applied between electrodes 50. The magnitude of the electric field is between 1 and 10 volts per cm, and the time of its application is between 1 and 100 seconds.

Thus, at the beginning of the experiment, a single cavity 52 of the stationary plate 38 holds the sample and multiple cavities 54 of plate 40 for containing the separated fractions are aligned sequentially as follows. As shown only the cells with $\mu > x/Et$ are desired. In the separation step, the top sample cavity 52 is aligned with the bottom cavity 54, (A), the electric field pull all cells with $\mu > x/Et$ toward the positive (+) pole. In (B), the transfer step is shown, whereby 100% of the cells with $\mu > x/Et$, 50% of all other cells are pulled into the upper compartment or cavity 52. The bottom plate 40 rotates sealing thereinbetween and aligning the next bottom plate cavity 54 in alignment with the top plate 38. The new bottom plate cavity or chamber 40 contains no cells. Separation step (C) is repeated whereby all cells with $\mu > x/Et$ remain in the top chamber 52 with some nonconforming cells. All of the separated cells in the bottom cavity 54 are rotated in the second transfer (D) whereby another bottom cavity 54 is aligned with the top plate cavity 52. When the separation step is completed, the bottom plate rotates and separates the sample into two parts for later analysis. This procedure can be repeated in stages to enhance and to establish a history of the electrophoretic process. After approximately 10 transfers about 99% or more of the μ>x/Et cells are isolated in the top sample cell 52, and approximately 0.1% or less of the nonconforming cells remain in the last bottom cell 54 of the bottom plate 40. Of course, the degree of separation and/or purification is dependent upon several variables including concentration of the cells and number of transfers; however, the number of cavities can be modified to obtain the desired results. For this prototype design, the capability to utilize up to 22 stages or more if required.

Figure 7:
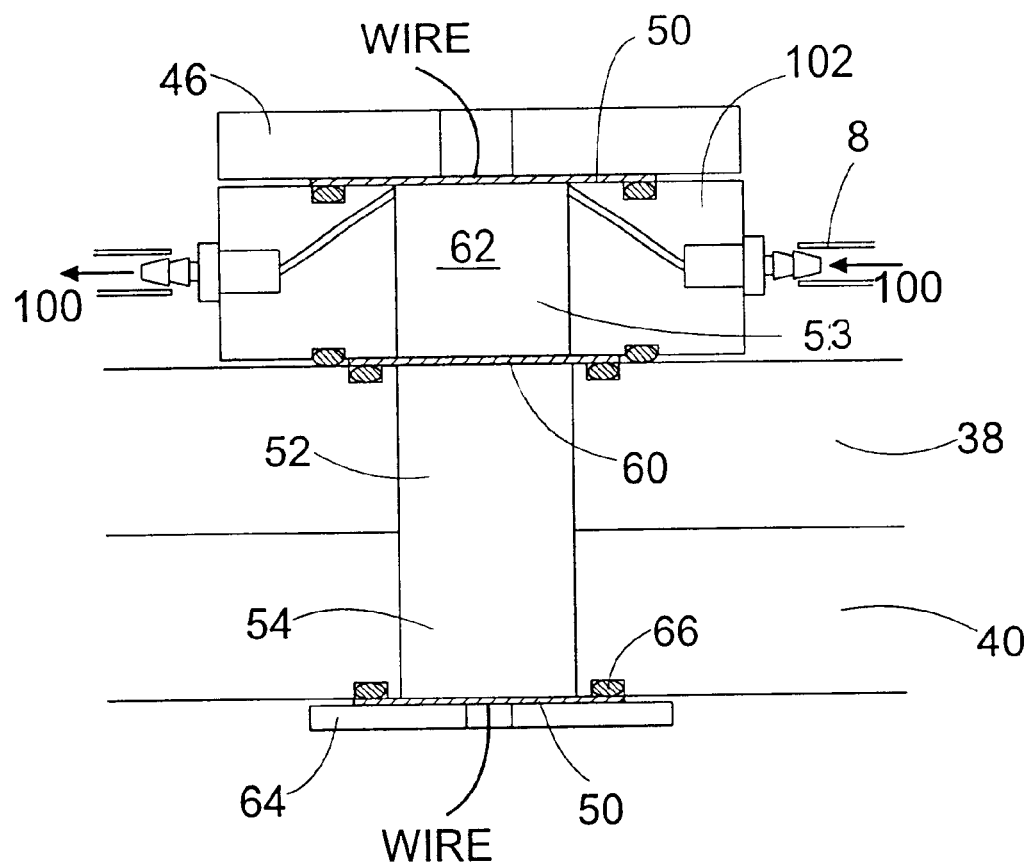
FIG. 7 is an elevation view of a pair of cavities in which electrophoresis takes place and a stationary electrode chamber for flowing electrolyte.

The rotating plate 40 will have at least 1 and preferably a plurality of chambers 54. In a preferred embodiment the rotating plate 40 has 22 chambers, and the stationary plate 38 which can also have an undetermined number of chambers 52 will has only 1 chamber, but typically may have four or more. Since the plate 38 with 1 chamber is exposed to the electric field during every stage, gases will accumulate at the electrode and the temperature of the fluid will rise significantly if not controlled. The plate configuration is shown in FIG. 7 with a simplied view of the cross section of the plates when the chambers are aligned. An optical ring can be used with the preferred embodiment to accomplish alignment wherein a reflective ring used in combination with an optical sensor provides means for aligning the cavities 52, 54 (cuvettes) at particular selected sites so the bottom rotary plate 40 port(s) 54 corresponds to one or more selected cavities 52 in the top stationary plate 38.

The plate arrangement is set forth in FIG. 7 shows a top and bottom plate, 38 and 40, respectively, with the electrolyte block and the electrical connections. The preferred electrolyte solution is a salt solution such as sodium chloride or preferably potassium chloride because they are good conductors. The electrolyte draws bubbles through the a membrane and carries them away where they are removed and float in an earth environment or are removed by a scrubbing apparatus in a space environment. The removal system may also contain filtering elements. The palladium disc or wire within each cavity also has the ability to removes hydrogen gas and prevents the collection of gases which form bubbles which interferes with the fluid flow, mass flow rate, temperature control, and quantitative measurements.

By experimentation, it was determined that when gases form at the electrodes 50, the electric field may be disrupted. A temperature change also affects the results of the separation process. To remove the gases and maintain an isothermal condition, an electrolyte coolant 100 contained within an electrode block 102 disposed in alignment with and over the cavity 53 of top stationary plate 38 providing coolant to be circulated around the electrode 50. Coolant is only needed on the electrode 50 of the top chamber(s) 52, and not the chambers 54 within the plate 40. The electrodes 50 are made of metal. Moreover, the preferred metal of composition for the electrodes 50 is Palladium which is a non-corrosive metal that has a unique property of absorbing hydrogen up to 400 times its own volume which also aids in gas removal.

Figure 17:
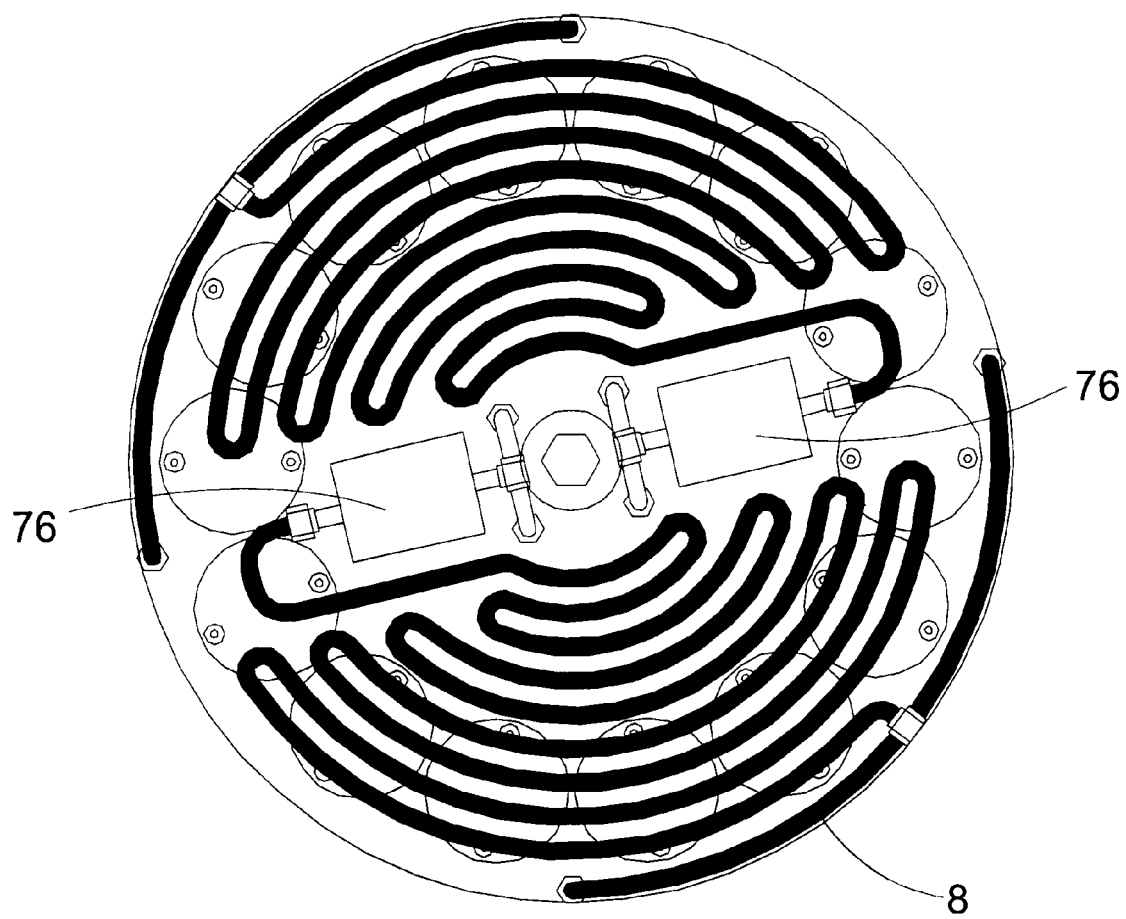
FIG. 17 is a top view of the device showing the pumps, feed reservoir, and circulation system for circulating coolant electrolyte to one or more selected cavities in the top stationary plate removing gas and heat, helping to maintain an isothermal process.

The selected coolant is preferably an electrolyte solution to avoid interrupting the electric field. The maximum conductivity of the electrolyte used for this purpose is approximately 10 ms/cm. The electrolyte used could be the same as the buffer solution in which the particles are contained. A lower conductivity buffer and electrolyte could be used. In a preferred embodiment, the upper separation chamber 52 is served by a chemical electrode 50 in which the electrolyte 100 also serves as a coolant. The electrolyte flow rate is sufficient to carry away the gases and heat. This flow rate can be as low as 10 ml/hr. or even discontinued when necessary. The method of cooling provides a method of controlling the flow rate while regulating fluid pressure. FIG. 17 illustrates the pump, feed reservoir, and circulation system for circulating coolant electrolyte to one or more selected cavities in the top stationary plate.

In one embodiment, each chamber is 0.275" tall and 0.375" in diameter. When the two chambers align, the sample is 0.550" tall and 0.375" diameter, having a total volume of 0.061 in$^3$ (1-ml). The electrodes 50 in the plate 40 with 22 chambers 54 are in direct contact with the sample solution. The single electrode 50 sits in a cavity that is 0.275" away from the sample solution. It makes contact with the circulating electrolyte. The electrolyte 50 is separated from the sample solution by a thin membrane 60, preferably a hydrophilic polymeric membrane. This membrane 60 should have negligible effects on the electric field, but will allow gases to escape from the chamber and pass into the electrolyte stream. The membrane 60 is rated up to a 3000 molecular weight cut-off.

An uniform electric field test was conducted to determine whether the electric field is affected by the presence of the membrane by observing the conductivity changes and voltage drops across the field as a function of time and bubble formation. The results indicated that there is no statistical difference in the voltages with or without the membrane in place for the first 10 minutes of the experiment and very little difference thereafter; and that there is very little variation in the electric field from the center to the edge of the chamber.

The expected range of conductivity in the sample solution is 200 mS/cm to 10 mS/cm. The highest necessary electric field at the greatest conductivity is 5 V/cm. Conductivity changes slightly due to gas build-up in the electrolyte, temperature, and particle separation are unavoidable, but increasing the voltage accordingly at the electrodes can minimize their impact. A voltage regulator circuit is shown in FIG. 9 to compensate for the changes in conductivity. The power input requirement is 12 VDC regulated at 1 amp. The maximum electrode voltage potential is limited to approximately 24 VDC due to restrictions on space shuttle and space station to conserve power. For earth laboratory use the voltage can be determined depending upon the particular power sources available. Based upon the conductivity values of the solutions, the voltages are regulated so that the desired electric field is maintained in the buffer, despite any overall conductivity changes due to heating, gassing, or ion migration.

An experiment was also conducted by filling the test sample chamber with a 50–50 mixture of pure phosphate buffer and a prepared suspension of 9.7 micron particles in phosphate buffer. After connecting the bottom electrode to the positive terminal and the top electrode to the negative terminal, power was applied until a clear front was observed at the region where the two blocks that form the sample cavity are joined together. It was determined that the particle movement was uniform indicating the electric field is uniform. It was also determined that the accumulation of bubbles in the cavities could interfere with the electric field which would effect the flow pattern.

Figure 8:
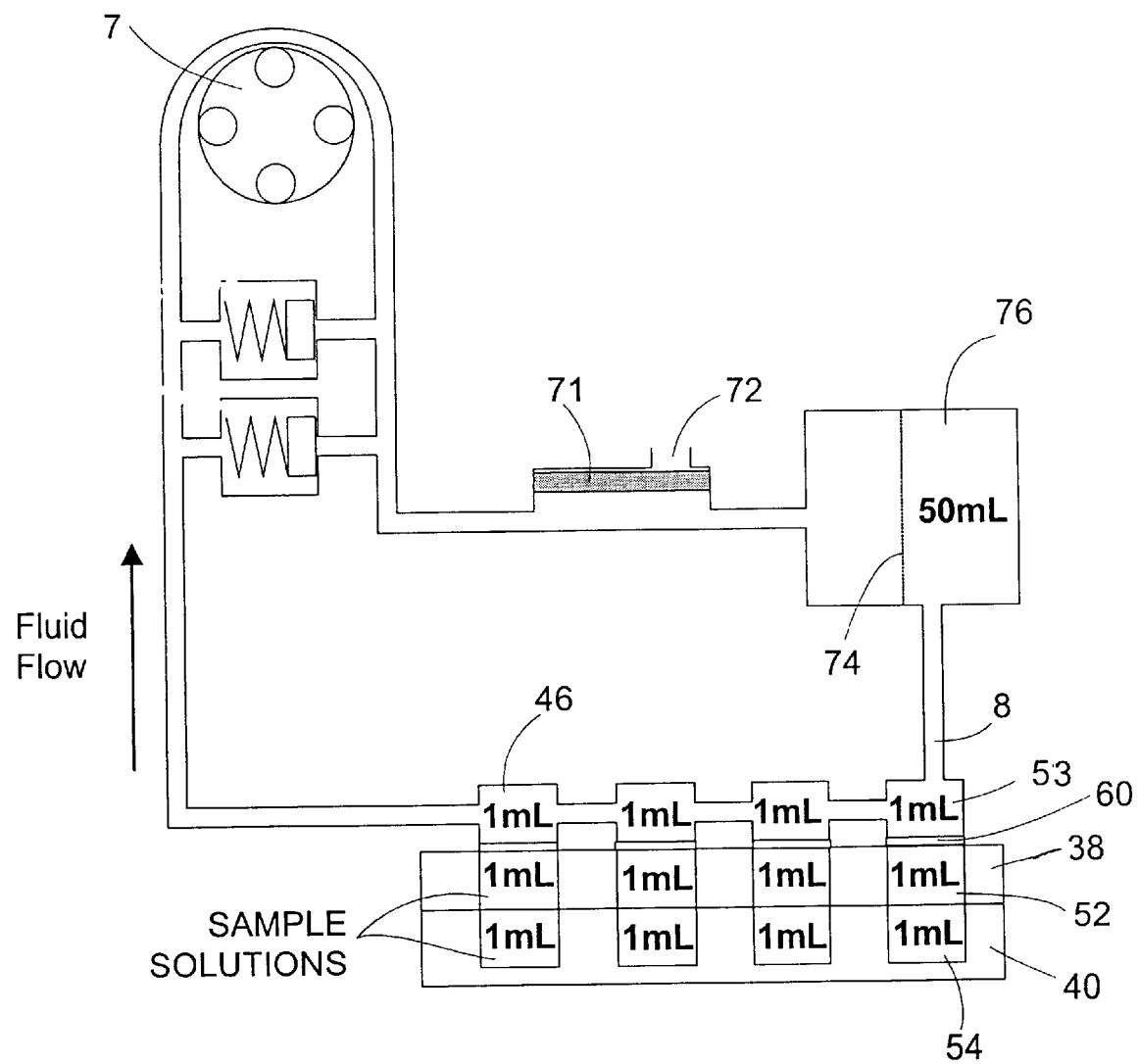
FIG. 8 is a diagram of the flow path for electrolyte fluid for the stationary electrodes in a high-current embodiment of the device shown in FIG. 2.

The circuit that controls the plate voltage has a potentiometer available for the user to manually control the current. A test point is accessible which gives the user the ability to calibrate the current accurately. In an automated embodiment, the processor-driven control circuit accomplishes this calibration. A switch operated manually or by software, can be utilized to reverse the electrode polarity. There are two general types of embodiments, a high current and a low current unit. The high current unit is based on the flowing electrolyte concept as shown in FIG. 8, while the low current unit has only metal electrodes.

A sealed interface between the two plates is provided having at least some face angle and preferably a face angle of between 0.1 and 10 degrees, and preferably about 1 degree on each plate to compensate for flexing and maintenance of the seal; however, having a face angle is not a requirement. As an alternate design or combination design one plate may be made thicker to lessen the effects of flexing. The face angle on that plate can be 0 degrees and a smoother surface can be obtained during machining; however, the face angle may be utilized at about 1 degree.

Figure 18:
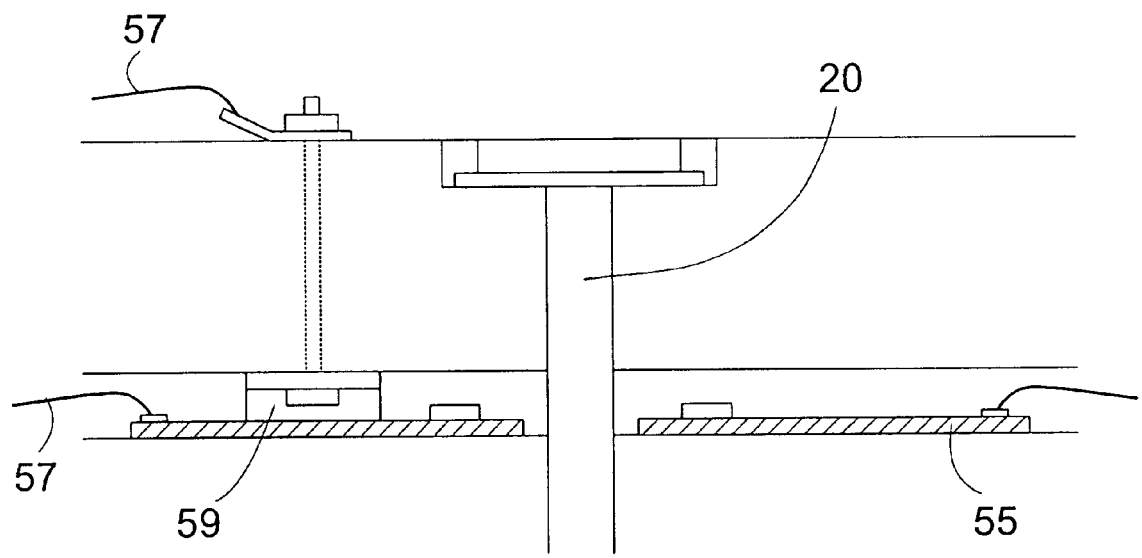
FIG. 18 is a side view showing the slip ring assembly for transferring electric current to the plates.
Figure 18:
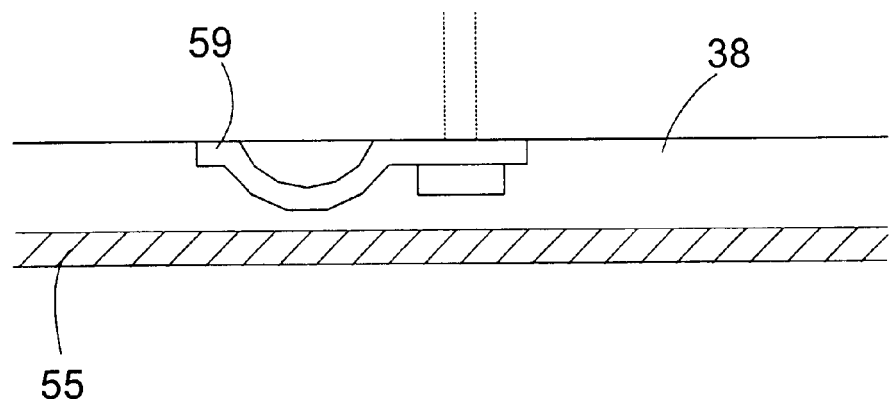
Figure 19:
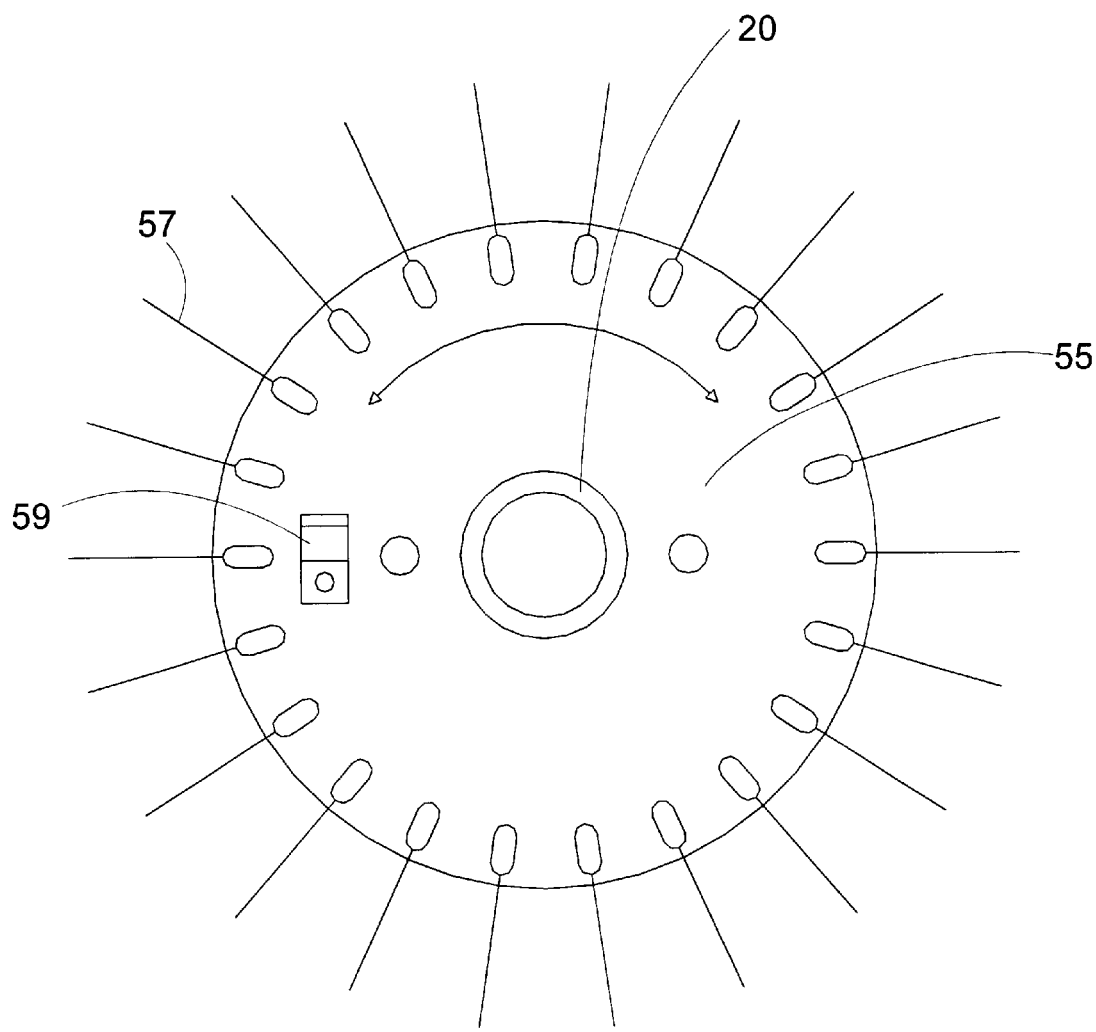
FIG. 19 is a top view of a slip ring wiper array for communicating with a rotating copper contact.

A sealed slip ring is installed within the rotating plate 40 to allow for 360+ degrees of movement, thus eliminating the need to flex wires during operation. FIG. 18 shows the slip ring assembly for transferring electric current to the plates and FIG. 19 illustrates a slip ring wiper for communicating with a rotating copper contact. As shown the conductive washer 55 rotates around the central axle 20 and is supported thereby. A plurality of wires 57 connected to electrodes 50 are in electrical communication with a washer 55 which is in electrical communication with a corresponding wiper 59 mounted to the top plate connected to the voltage supply circuit via a conducting screw which penetrates the top plate 38. Thus, the wires 57 carry current from the conductor washer 55 to electrodes 50 of the bottom plate 40.

A linear actuator on a syringe supplies the flow of electrolyte. The pressure fluctuations are suppressed by the flexible hosing (tubing). The pressure in the electrolyte collection cavity 54 will be slightly lower than the sample cassette chamber 52. This facilitates the gases passing through the electrode membrane 60. A suction pump can maintain the pressure gradient in the electrolyte. Depending on the direction of flow, one syringe creates suction while the other supplies fluid so that it is possible to create a higher pressure or approximately equal pressure (electrolyte vs. sample pressure). A peristaltic pump or piston is used for electrolyte circulation. The electrolyte pumping rate can be varied by adjusting a potentiometer. Pumping can be controlled automatically or pumping may be automated.

A DC gear drive motor pumps the fluids and a worm gear drive motor assembly rotates the bottom plates 40.

The unit 30 also can be adapted to be held by a mounting bracket which will allow the user to position the plates in any orientation (on side, face up, or face down). Since gases rise in a liquid when subjected to gravity, the membrane 60 will be positioned on the top of the chamber for nearly all ground-based tests. The plate mounting bracket pivots to allow for this. This feature is not available (or needed) on the flight prototype.

As shown in FIG. 10, an embodiment of the device of FIG. 2 adapted for functioning in space flight showing the electrophoretic device 30 nested within a cassette 110 which is inserted within a containment enclosure 80. Within the cassette 110 is the base 19, a stepper motor, electrolyte reservoir 76, indexing tray, stationary sample plate 38, rotating plate 40, circuit board 83, collection plate, and electromagnet holding magnet.

Operating Models

As in equilibrium-stages separations, two operating models have been selected on the basis of the properties of the specific separands to be separated, a constant-potential model and a pseudoequilibrium model.

The constant-potential model and the pseudo-equilibrium model enables the user to calculate the optimum duration for applying the electric field in order to obtain maximum purification. Additionally, it enables the use to calculate the number of successive purification operations (stages) to which the original mixture would have to be subjected in order to obtain the desired level of purity.

In the constant-potential model two different types of particles are tracked from on cavity to the corresponding cavity on the other plate. The transport of particles by electrical fields is a rate process (not an equilibrium process) and the particles having higher mobility are separated faster when compared to those having relatively lower mobility. In a counter current distribution (CCD) apparatus, the separation of particles having different electrophoretic mobility is achieved by contacting the buffer solution of the top chambers with the bottom chambers containing the particles in buffer by applying an electrical field at regular predetermined intervals. A CCD apparatus has n extraction stages. Let us consider a situation where the bottom chambers of each of these stages have (say) two types of particles with electrophoretic mobilities $\mu_1$ and $\mu_2$.

The number of particles initially (at t=0) present in the bottom chambers is denoted by N, and the change in the number of particles in a chamber n after step r will be equal to the number of particles that migrate to the top chamber during step r. The general equation can thus be written for this situation as a material balance:

$-[x_1N]_{n,r}+[x_1N]_{n,r-1}$=Number of particles migrating from stage n during step r, to the top chamber (1) where N is the total number of particles present in any of the n bottom chambers, $N_1$ the number of particles with mobility $\mu_1$, $\mu_2$ the number of bioparticles with mobility $\mu_2$, $N=N_1+N_2$, and $x_1=N_1/(N_1+N_2)=N_1/N$ Now let us consider one chamber, with total depth D and radius R having particles suspended in buffer solution. When an electric field is applied the particles move due to their corresponding electrophoretic mobilities. Their velocity will be proportional to the field applied:

$$\frac{dy}{dt} = \mu E \qquad (2)$$

and the proportionality constant m is electrophoretic mobility of the bioparticle, and thus the characteristic of the bioparticle. Its magnitude is decided by the surface charge of the bioparticles. Integrating between the limits y=0 to D and t=0 to t, where t is the time of application of electric field, results in D=$\mu$Et.

In other words, for the particle of mobility $\mu$ to move a distance D, an electric field of intensity E must be applied for a time t. It is obvious that if E is increased, t will decrease or vice versa, under otherwise similar conditions.

Initially the particles are randomly distributed over the volume of the lower chamber. However, their probability of migrating/moving to the top chamber increases as their distance from the bottom of the chamber increases. At any given set of experimental conditions of E and t. For example, the number of particles that migrate to the top chamber will be four times higher if they are at D/4 location (from the top surface) in the chamber when compared to those at location D. That is, the ratio of these heights gives the relative number to the bioparticles that migrate to the top chamber at any given set of E and t. To arrive at the absolute number, this ratio has to be multiplied by the concentration of the particles (i.e., number of particles per unit volume) since the ratio of the heights is nothing but the ratio of the volumes of the chamber corresponding to the location considered. Therefore, the number or particles migrating during step r is, for example, $$\frac{(\mu E \tau \pi R^2)}{(D/2) \pi R^2}(N_1)_{r-1}$$

In order to capture ½ of the particles with mobility $\mu$ in the first transfer. Now Eq. (1) becomes $$-(x_1 N)_{n,r} + (x_1 N)_{n,r-1} = [2\mu E t (N_1)_{r-1}]/D$$

where $(N_1)_{r-1}$ is the number of particles of mobility $\mu$ per unit volume in stage n at step (r-1).
Hence, $$(x_1 N)_{n,r} = [(\mu E t)/(D/2)](N_1)_{n,r-1} + (x_1 N)_{n,r-1} \quad (3)$$

Figure 20:
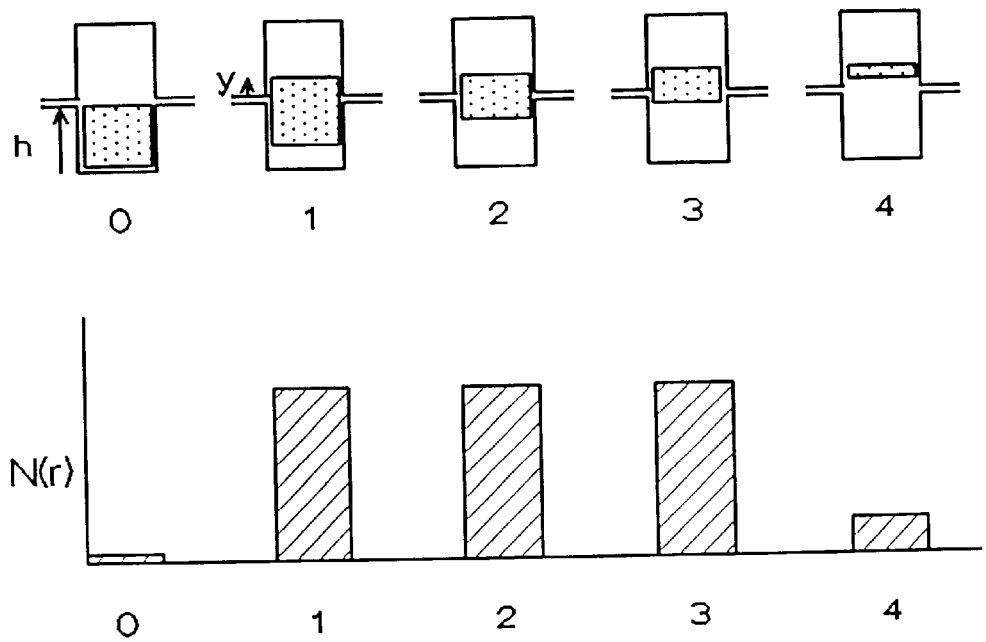
FIG. 20 shows a schematic representation of the migration of particles of a single type from the original single stationary cavity to a series of rotary cavities during the application of a fixed electric field for a fixed period of time per stage (constant Ef), representing the constant-field operating model.

This is a general equation which enables us to estimate the fraction of particles having a mobility of $\mu_1$, at any stage, provided their concentration is known in the previous stage. Similar equations can be written for particles having other mobilities. Note, however, that the particles are assumed to be in the upper half of the bottom chamber. Equation (3) needs to be modified to make the equation more general. Assuming that the particles are uniformly distributed in the chamber, then, in general, $$(x_1 N)_{n,r} = -[(r)(\mu_1 E t)/(D)](N_1)_{r-1} + (N_0) \quad (4)$$

where r is the step number and is the initial concentration of the particles having mobility. An example of a predicted migration pattern and a distribution of particles in fractions based on Eq. (4) is shown in FIG. 20.

3.1.2 The Pseudoequilibrium Model

In the pseudoequilibrium model it is assumed that the optimum potential is applied at each stage for separation of a pair of separands. In other words, if the mixture that is to be to separate by electrophoresis has two types of particles with different mobilities, all particles (of both types) could be drawn into one stage if the current were applied long enough. The primary objective was to determine the time for which the driving electric potential was to be applied in order to achieve a maximum resolution and the actual value of this maximum resolution that can be obtained. This optimum resolution is designated "pseudoequilibrium" for the particular stage of the process. The next goal was to figure out how to further enrich the mixture obtained from the previous process, and keep doing this in a stepwise manner. In terms of a classical chemical engineering separation process, this equivalent to calculating the operating line. A corollary to calculating the operating line is the development of protocols which outline the handling of the various fluids and mixtures. This was done for the most general case—when it is preferred to isolate some types of particles and discard other types from a suspension with many different types of particles.

Since the process of electrophoresis has not been operated in a multistage manner before, there is no established convention of defining and mathematically representing the various physical parameters that are encountered in a multistage electrophoresis. Before describing the mathematical model, a short overview explaining the rationale behind what physical parameters have been chosen to be monitored during the process, the designating of the parameters, and symbols representing same. The concepts and definitions applicable are presented for the simplest of cases—wherein the mixture that is to be resolved contains only two types of dissolved particles (say, of types A and B). Typically, at the beginning of the electrophoretic separation in each of the chambers thus formed, one of the halves contains a mixture of particles whereas the other one contains clear fluid. The former is called the "feed" and the latter the "solvent". If allowed, the separation takes place for a certain amount of time, and the feed would be depleted of particles of a particular type (say type A). It can be defined as "residue". The solvent now would be enriched with these particles of type A and is now called the "extract". The extract from the final stage, which meets our required degree of purification, is called the product. The original mixture of particles is called the "crude". The crude serves as the feed for the first stage.

The desired objective is to obtain a suspension containing only (or almost only) the particles of our desired type. As long as there are particles of only that type present, its actual concentration (i.e., in terms of the number of particles per unit volume of suspension) is not critical. It is not particularly useful if we are able to obtain a high number of our desired particles in a sample if it is accompanied by large numbers of other particles. It is of value to chose to monitor the particle fraction of a given type of particle, just as in the case of the constant-potential model described above. In the two-particle-type case a particle fraction of particles of type A is defined to be the ratio of the number of particles of type A in a given volume of liquid, to the total number of particles.

A stage and the concept of pseudoequilibrium is defined as follows: In a classical equilibrium-driven process, a theoretical stage is usually defined to be completed when the extract is in equilibrium with the residue. However, since electrophoresis is kinetically driven process, theoretically all the particles suspended in the feed may be transferred to the extract. In the mathematical analysis which follows, it is shown that for a given particle fraction of A in the feed, there exists an optimum duration for applying the driving potential gradient. The degree of separation achieved actually decreases if the potential is applied for a longer duration. Thus, the "pseudoequilibrium" for the separation is the to have been reached when this maximum possible degree of separation is achieved. As a consequence, each "stage" in this process is completed when pseudoequilibrium is achieved between the residue and the extract.

Upon specification of the following physical parameters: $x^3_{A5}$ represents the particle fraction in the feed or the residue; Y represents the particle fraction in the solvent or the extract. A letter in the subscript shows the particle type. The number in the superscript tells us the chamber number whereas the number of the electrophoretic process. Thus, $X^3_{A5}$ represents the particle fraction of type A in the $3^{rd}$ chamber prior to the $5^{th}$ stage of separation. $Y^{*3}_{A5}$ represents the particle fraction of type A in the $3^{rd}$ chamber prior to the $5^{th}$ stage of separation. (The asterisk implies that pseudoequilibrium has been achieved). $Y^{*3}_{A5}$ represents the mobility of a particle of type A; and $m^2_{A4}$ represents the number of particles of type A actually transferred during the $4^{th}$ stage in chamber 2 from the feed to the extract.

Let the volume of each chamber be equal to 2V and let the crude be such that a total of P particles is suspended in fluid of volume V. This crude serves as the feed to the first stage in chamber 1. If $X_A$ is the particle fraction of particles in the feed, which has a total number of particles equal to $P_O$, then $P_{AO}$ is the number of particles of type A in the feed given by $$P_{AO} = (X_{AO})P_O \tag{5}$$

Similarly, $$P_{BO} = (X_{BO})P_O \tag{6}$$

Now, if an electric field of strength E is applied for a duration of time t, the number of particles of each type that is transferred into the extract is given by $$m_{Ai}^j = (X_{Ai}^j)P_{-1}\frac{\mu_A E t}{H} \tag{7}$$

$$m_{Bi}^j = (X_{Bi}^j)P_{-1}\frac{\mu_B E t}{H}$$

As a consequence of this transfer, the particle ratio of particles of type A is given by $$Y_{Ai}^{*j} = \frac{m_{Ai}^j}{m_{Ai}^j + m_{Bi}^j}$$

which, on simplification, reduces to $$Y_{Ai}^{*j} = \frac{X_{Ai}^j \mu_A}{X_{Ai}^j \mu_A = X_{Bi}^j \mu_B} \tag{8}$$

which says that this is the particle fraction to be found in the extract irrespective of the duration of the application of the electric field. However, this equation assumes that there are particles of all types in the feed/residue. However, if $\mu_A > \mu_B$, there will come a time when all particles of type A would have been transferred to the extract and there would be only particles of type B remaining in the residue. It would be logical to stop the application of the electric field at this point. This duration of time is found by setting $$m_{Ai}^j = P_{Ai}^j \tag{9}$$

which, on simplification using Eq.(7), yields $$t = \frac{H}{\mu_A E} \tag{10}$$

At this time, pseudoequilibrium is reached in stage j. At pseudoequilibrium, the particle fraction of particles of type A in the extract is given by Eq. (8), which on further simplification yields $$Y_{Ai}^{*j} = \frac{1}{\left(1 - \frac{\mu_B}{\mu_A}\right) + \frac{1}{X_{Ai}^j}\left(\frac{\mu_B}{\mu_A}\right)} \tag{11}$$

At this stage note that (i) this duration of time is independent of the feed concentration; (ii) if interested in isolating pure B (without regard for yield), it is possible to draw off pure B at this point as the residue has only particles of pure B suspended in it; (iii) the pseudoequilibrium particle fractions in the extract depend on only two things: the ratio of the electrophoretic mobilities of the two types of particles and the particle fraction of particles of type A in the feed (prior to the application of the electric field in that particular stage).

Figure 21:
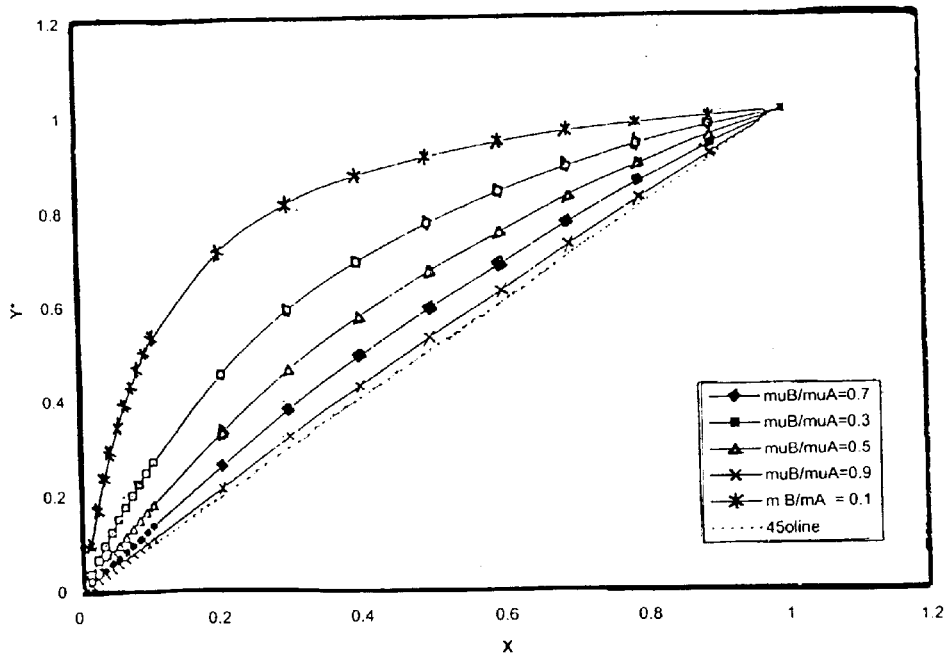
FIG. 21 is illustrates equilibrium lines for the separation of two separands having the indicated mobility ratios using the pseudoequilibrium model, Y, particle fraction in the extract, X, particle fraction in the feed, muB/muA, mobility ratio.
Figure 22:
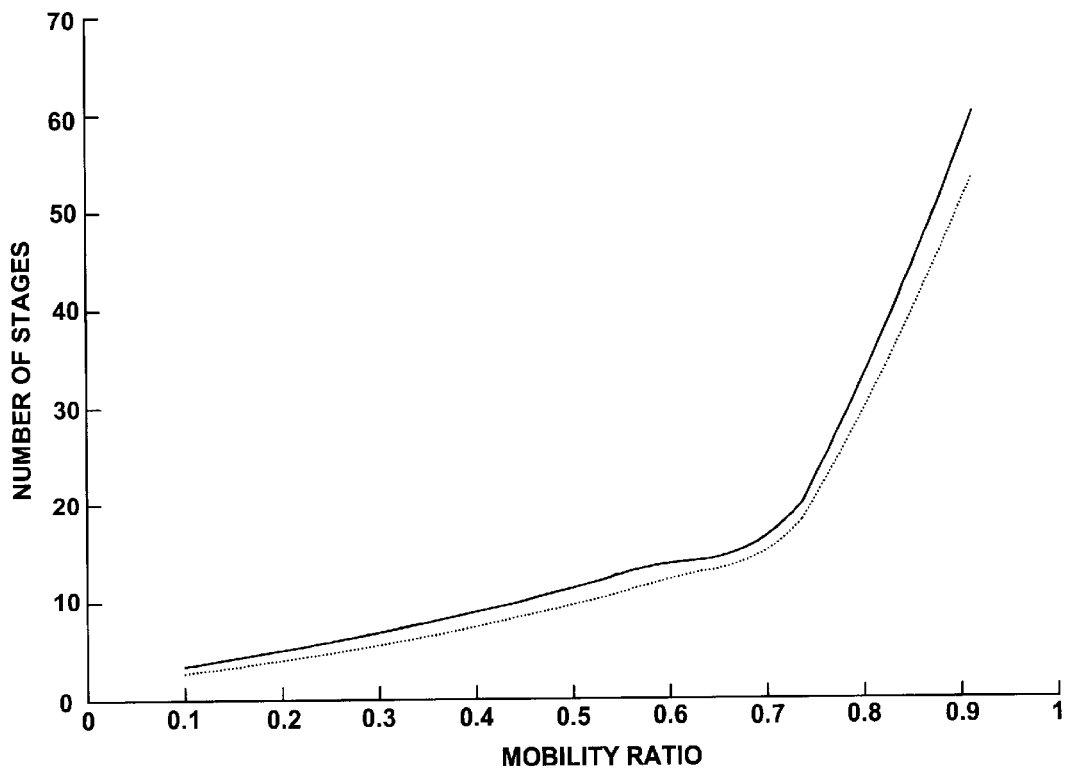
FIG. 22 is a graph of the Number of Stages v. the Mobility Ratio representing the purity resulting from application of the pseudoequilibrium model to the separation of two particle types with the given mobility ratios.

Pseudoequilibrium plots, which show the variation of the particle fraction in the extract with the particle fraction in the extract with the particle fraction in the feed for the particle with the higher mobility may thus be constructed for various values of the mobility ratio (ratio of the electrophoretic mobility of the shower particle to that of the faster particle). FIG. 21 shows such plots for mobility ratios varying from 0.1 through 0.9. Once the (pseudo)equilibrium lines have been obtained, the next step is to develop an operating line. The operating line would be a graphical representation of the equation which tells us what the particle fractions of the feed are as a function of the particle fractions of the extract from the previous stage. Several possible modes of operation can be considered for this system. Initially the mode of operation was to chose the mode of using the extract from one stage as the feed for the next. In this case the operating line corresponds to the next. In this case the operating line corresponds to the 45° line in the pseudoequilibrium plot, and the number of stages is found by stepping off the stages in a way similar to classical methods such as the McCabe Thiele method [16]. FIG. 22 shows the variation in the number of stages required to take the particle fraction of the more mobile particle from 5 to 95% as a function of the mobility ratio.

3.2 Thermal Model

Figure 11:
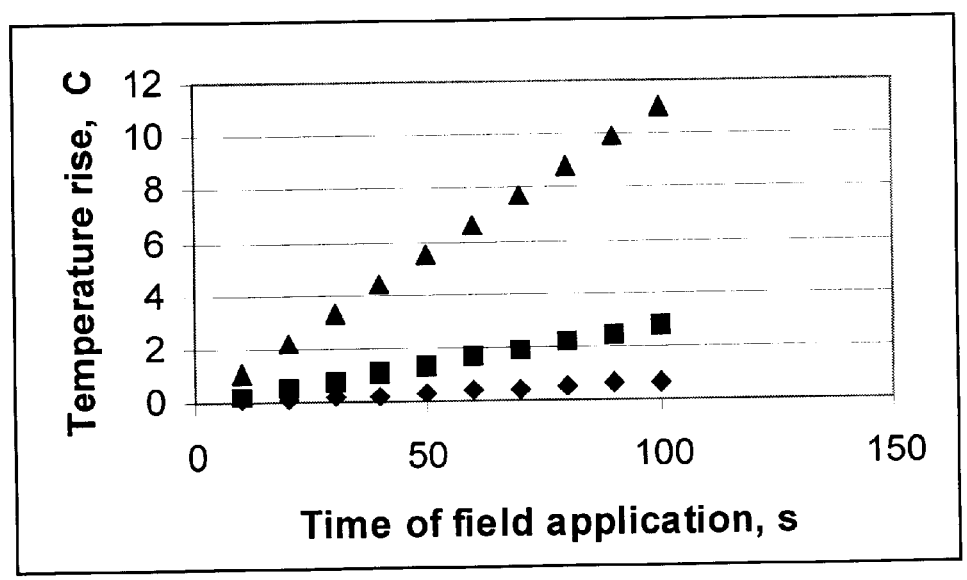
FIG. 11 is a graph showing an experimental result of the number of particles extracted at constant potential as a function of the collecting cavity number with the temperature rise in degrees C. and versus the time of field application in seconds depicting heating curves for a single cavity due to application of field strength to a cavity containing 0.01 M phosphate buffer, Squares, 5 V/cm calculated from Eq. (12) triangles, 10 V/cm calculated from Eq. (12), shown in diamonds, measurement with a thermistor in the cavity during application of a 5 V/cm field.

When low-conductivity buffers are used, rejection of heat to ambient conditions is adequate; however, when a current of several mA must be applied, active heat rejection is required, and this can be achieved by using a recirculating electrode buffer system [10,12]. Initially it was desired to determine the rate of sensible heat generation due to passage of current through a pair of cavities with bare Pallidum (Pd) electrodes. The rate of temperature rise in an adiabatic cavity depends on the buffer conductivity and the desired electric field strength and can be determined from $$dT/dt = IE/p\,C_p \tag{12}$$

where I is the current density, E the field strength (=I/k), p the solution density, $C_p$ the specific heat of water at 25° C. (assumed constant) and k the conductivity. Two conditions were considered: field strengths of 5 and 10 V/cm in 0.01 m phosphate buffer. The former case, for example, for Eq. (12), results in $$dT/dt = 0.022\,deg\,C./s$$

and this is plotted as squares in FIG. 11. A similar plot for 10 V/cm shows the sensitivity of heating upon the field and indicates that using higher fields or higher conductivities will require the implementation of a cooling system. The generation of sensible heat was monitored in a single cavity using a small thermistor probe; the results are plotted as diamonds in FIG. 11. The corresponding relationship is only dT/dt=0.022degC./s, indicating that about ½ of the heat was rejected to the ADSEP polycarbonate plate. These calculations apply only to cavities with bare Pd electrodes, and heat transfer relationships developed for electrodes with circulation and cooling will be published later.

3.3 Particle Migration Experiments

Figure 12:
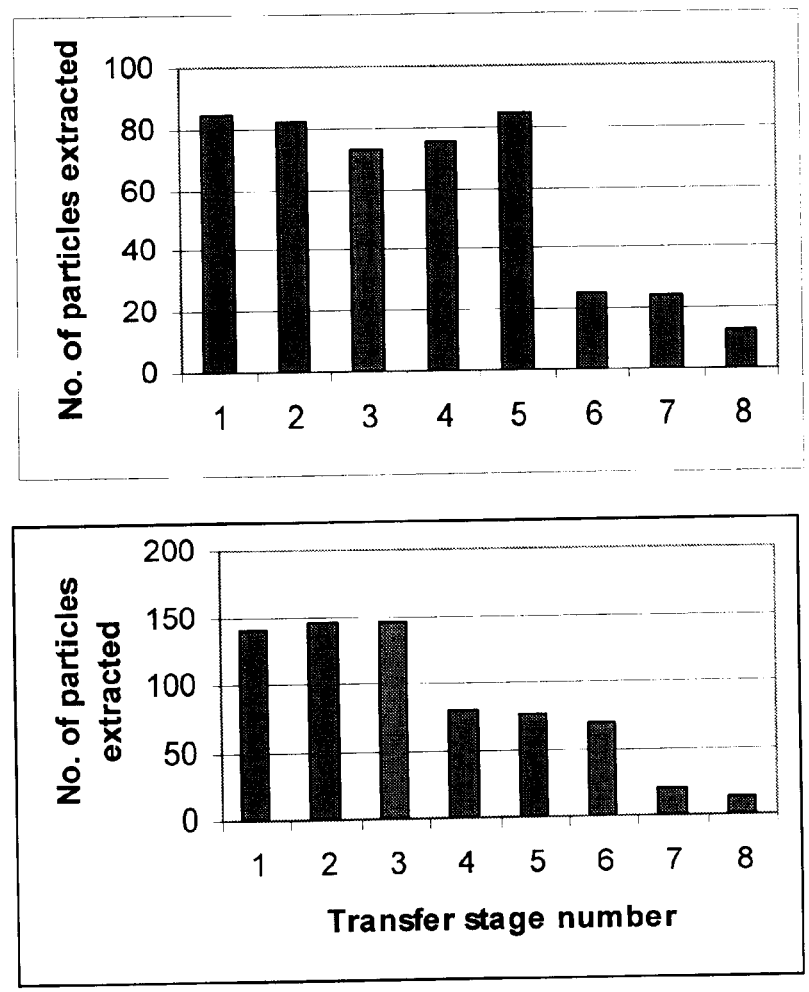
FIG. 12 is a graph showing the pseudoequilibrium concentration of a separand vs. its concentration in the feed fluid, with the path to purity at pseudoequilibrium stepped off at each stage, beginning in the upper right, wherein the results of a preliminary single particle migration experiment in a test of the constant-potential model for comparison with FIG. 20, and the top graph, 5 V/cm, the lower graph, 10 V/cm in 0.01 M phosphate buffer, Ph8.0, ordinate units, $10^4$ particles/mL.
Figure 13:
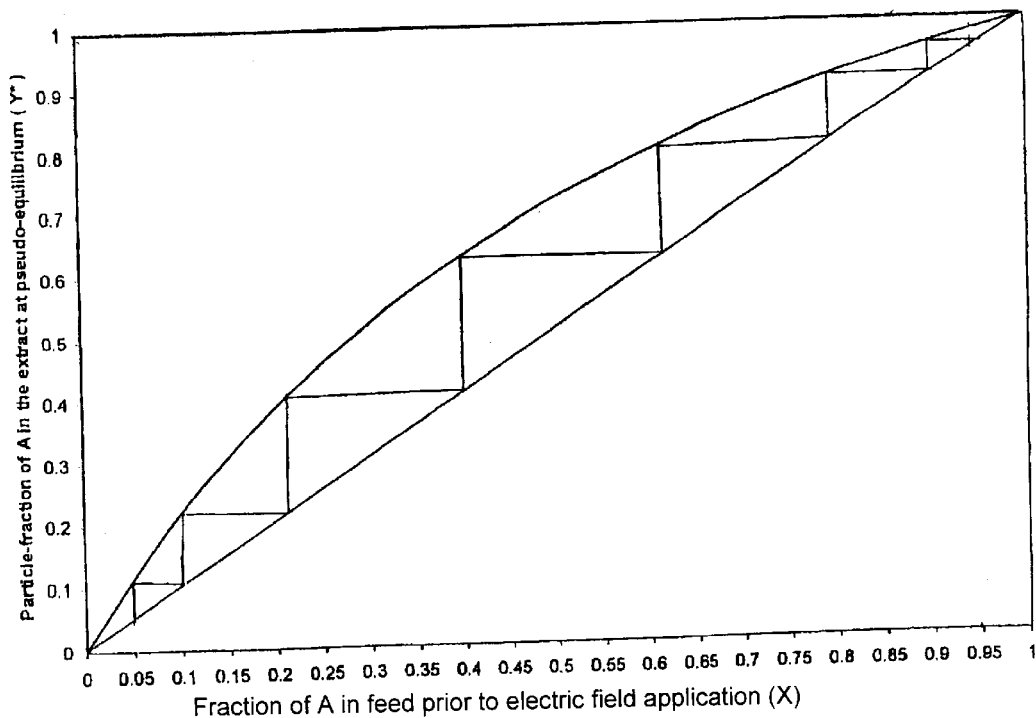
FIG. 13 is a graph showing the rise of temperature during application of a current to a pair of cavities based on adiabatic theory and experiment.

When a suspension of particles was placed in a single bottom cavity of the unit and a field was applied (5 or 10 V/cm) for 1 min per cavity, the resulting fractograms compared favorably with model predictions. The constant-potential model was tested in a series of experiments using 3.4 $\mu$m sulfated polystyrene latex particles (Interfacial Dynamics, Portland, Oreg.) as test particles. The initial concentration was $5.5 \times 10^6$ particles/mL, and field strengths of 5 or 10 V/cm were applied for 60 s per transfer for eight transfers. The results of two such experiments are shown in the bar graphs of FIG. 12: when the field strength was doubled, the cell extraction was completed in about half the number of transfers. Specifically, $450 \times 10^4$ particles were extracted in six transfers at 5 V/cm, while the same number was extracted in three transfers at 10 V/cm, in keeping with Eq. (4) and as described in FIG. 20.

Charged-Solute Concentrator

In yet another embodiment the multistage separator 10 can be configured as a charged-solute concentrator. In this embodiment the sample cuvette and one collecting cavity, the first collecting cavity, are placed in contact and filled with a volume of liquid containing a solute that is to be concentrated. The solute may be small molecules, a protein, nucleic acid, drops, particulate matter or whole biological cells or their components. It is only required that the solute have a net electrical charge when dispersed in the volume of liquid. Electrodes, as described in other embodiments, are energized so that all of the solute in the combined cavities travels into the first collection cavity. The first cavity is translated so as to be contacted with a second collecting cavity in the opposite plate, the collecting cavity having less volume than the first collecting cavity. Electrodes, as described in other embodiments, are energized so that all of the solute in the first collecting cavity travels into the second collection cavity. The second cavity is translated so as to be contacted with a third collecting cavity in the plate opposing it, the third collecting cavity having less volume than the second collecting cavity. Electrodes, as described in other embodiments, are energized so that all of the solute in the second collecting cavity travels into the third collection cavity. And so on until the final concentration desired by the operator is reached.

It should be obvious to those practiced in the art that the process can be repeated any number of times. All numbers of repetitions of this process are considered protected by the present patent.

EXAMPLE 1

Charged-Solute Concentrator Charged-Solute Concentrator

An enzyme solution, 1.0 mg/ml in concentration and 1 ml in volume, is placed in the combined sample cuvette (having volume of 0.5 ml) and first collecting cavity (having a volume of 0.5 ml). A field of 5 V/cm is applied for 10 minutes. All of the enzyme in solution is moved to the first collecting cavity, and its concentration is now 2 mg/ml. This solution is contacted with an opposing, second collecting cavity that is 0.25 ml in volume. All of the enzyme is next transferred electrophoreti-cally to this second collecting cavity, and its concentration is now 4 mg/ml. This solution is next contacted with an opposing, third collecting cavity that is 0.125 ml in volume. All of the enzyme is next transferred electrophoretically in 10 minutes to this third collecting cavity, and its concentration is now 8 mg/ml. In this manner an 8-fold concentration of the enzyme has been achieved, which is a typical goal in biochemical processing. In this application the present invention performs an equivalent concentration step in approximately ½ hour a task that requires overnight when dialysis is used, requires the adsorption of the enzyme to an adsorbent if adsorption (chromatography) is used, and requires precipitation or the enzyme if sedimentation is used.

The foregoing detailed description is given primarily for clearness of understanding and no unnecessary limitations are to be understood therefrom, for modification will become obvious to those skilled in the art upon reading this disclosure and may be made upon departing from the spirit of the invention and scope of the appended claims. Accordingly, this invention is not intended to be limited by the specific exemplifications presented hereinabove. Rather, what is intended to be covered is within the spirit and scope of the appended claims.

What is claimed is:

1. A multistage electrophoretic purification device for separating, collecting, and purifying cells, media, protein, and other particles contained in a fluid by subjecting samples of decreasing electrophoretic mobility to an electric field of selected strength causing migration of said particles and collecting said particles in a plurality of collection cavities providing multistage extraction, said multistage electrophoretic purification device, comprising:

a base;

a frame supported by said base a stationary sample plate supported by said frame having at least one sample cavity therein;

a rotating collection plate including a plurality of collection cavities in rotating sealed fluid communication and alignable with said at least one sample cavity;

means for providing an electric current;

means for rotating said rotating collection plate;

means for controlling the rotation of said collection plate;

an electrolyte fluid in communication with said at least one sample cavity;

means for pumping said electrolyte fluid in and out of said at least one sample cavity; and means for controlling said electric current in which the magnitude of the electric field is held constant at a selected field strength by a microprocessor controlled electric circuit.

2. A multistage electrophoretic purification process for separating and purifying cells, particles, and proteins, comprising:

a frame;

opposing circular plates defining a stationary sample plate containing particles to be separated in a fluid, and a rotating collection plate in cooperative sealable engagement with one another, each one including at least one cavity alignable with one another;

said at least one stationary sample plate cavity and said at least one rotating collection plate cavity positionable for fluid communication with one another arranged to form a multi-stage thin-layer extraction system;

said at least one stationary sample plate cavity and said at least one collection plate cavity containing a metal electrode for producing an electric field in said fluid subjecting said particles to be separated to said electric field separating said particles by their degree of electrophoretic mobility causing migration of said particles and collecting said particles in said at least one collection cavity;

whereby upon complete separation the electric field is de-energized and the plates are rotated countercurrently until the upper cavity aligns with a lower cavity with fresh solution that is thoroughly mixed with the separated cells or molecules, and the process is repeated as many times as necessary to effect the desired separation.

3. A method of separating cells, particles, proteins and other separands with an electrophoresis device comprising the steps of:
  placing a sample of particles to be separated comprising cells, media, proteins or other separands, or mixtures thereof into at least one sample container containing an fluid and supported by means for holding;
  rotating a collection plate having at least one collection cavity in sealed cooperative engagement with said at least one sample container;
  aligning said at least one collection cavity with said at least one sample container providing fluid communication therewith;
  applying an electric current field to said sample in said at least one sample container while said at least one collection cavity is in fluid communication therewith;
  collecting a fraction of said sample containing particles to be separated having a different electrophoretic mobility in said at least one collection cavity while said electric field is applied thereto.

4. The method of claim 3, including the step of holding the magnitude of said electric field constant at a selected field strength by a microprocessor-controlled electric circuit.

5. The method of claim 3, wherein said collection plate defines a circular disk.

6. The method of claim 3, including the step of maintaining the temperature at an isothermal state.

7. The method of claim 3, wherein said collection plate includes a plurality of collection cavities.

8. The method of claim 7 including the step of collecting samples of decreasing electrophoretic mobility in stages in said plurality of collection cavities while said electric field is applied to said sample particles to be separated in said at least one sample container in fluid communication in each of said plurality of collection cavities providing multistage extraction.

9. The method of claim 3, including the step of controlling said electrical energy input.

10. The method of claim 3, including the step of gravitationally stabilizing said electrophoresis device.

11. The method of claim 3, wherein said means for holding at least one sample container is disposed within a sample plate.

12. The method of claim 3, wherein said sample plate defines a circular disk.

13. The method of claim 3, including the step of disposing oppositely charged electrodes at the respective ends of said at least one sample container and said at least one collection cavity providing said electric filed creating a thin layer countercurrent distribution thereinbetween.

14. The method of claim 13, wherein said electrodes comprises a noble metal.

15. The method of claim 3, wherein said at least one sample container and said at least one collection cavity define disk shaped half cavities alignable for sealable fluid communication, said disk shaped half cavities having a depth of only a few millimeters.

16. The method of claim 8, including the step of skimming said particles to be separated from a top of a single collection cavity without mixing.

17. The method of claim 8, including the step of skimming said particles to be separated from a top of each collection cavity with remixing at each stage.

18. The method of claim 3, including the step of controlling the temperature of said fluid in a range of from between $-37°$ C. to $20°$ C.

19. The method of claim 3, including the step of collecting different types of cells.

20. The method of claim 3, including the step of collecting only cells, particles, media, or combination thereof.

21. The method of claim 3, including the step of providing a replenish able medium by means of perfusion which is programmable or active on demand.

22. The method of claim 3, including the step of collecting different types of cells.

23. The method of claim 3, including the step of providing an electromagnetic stirring system.

24. The method of claim 3, including the step of providing means for selecting solutions, temperatures, and sampling times.

25. The method of claim 3, including the step of providing means for collecting samples.

26. The method of claim 3, including the step of purifying said particles to be separated using a low conductivity separating buffer and electrode metals selected to prevent gas bubble release.

27. The method of claim 3, wherein said electrophoresis device is contained within a cassette.

28. The method of claim 11, wherein said sample plate comprises a nonconducting polymer.

29. The method of claim 3, including the step of providing an electrolyte in from an electrolyte reservoir in fluid communication with said at least one sample container.

30. The method of claim 29, wherein said electrolyte reservoir is separated from said at least one sample container by a hydrophilic polymeric membrane.

31. The method of claim 30, wherein said membrane comprises a molecular weight of less than 3000.

32. The method of claim 14, wherein said Nobel metal electrode comprises palladium.

33. The method of claim 3, wherein the electric current field is held constant at a selected field strength.

34. The method of claim 29, including the step of releasing gas bubbles formed in said electrolytic solution via a hydrophilic polymeric membrane in fluid communication therewith.

35. The method of claim 11, including the step of applying a nonvolatile and inert grease between said sample plate and said collection plate.

36. The method of claim 11 including the step of using an optical sensor and a reflective ring for aligning said at least one collection cavity with said at least one sample container.

37. The method of claim 29, wherein the electrolyte is selected from the group consisting of sodium chloride and potassium chloride.

38. The method of claim 29, wherein the conductivity of said electrolyte solution extends up to 10 mS/cm.

39. The method of claim 3, wherein the electric current field is no more than 5 V/cm.

40. The method of claim 29, including the step of providing a selected positive or negative pressure gradient between said at least one sample container and said electrolyte reservoir.

41. The method of claim 3, including the step of utilizing a constant-potential model for enabling the user to calculate the optimum duration for applying the electric field to said sample to be separated in order to obtain maximum purification.

42. The method of claim 3, including the step of utilizing a pseudo-equilibrium model for enabling the user to calculate the optimum duration for applying the electric field to said sample to be separated in order to obtain maximum purification.

* * * * *